US008114599B2

(12) United States Patent
Meagher et al.

(10) Patent No.: US 8,114,599 B2
(45) Date of Patent: Feb. 14, 2012

(54) COMPOSITIONS AND METHODS FOR FREE-SOLUTION CONJUGATE NUCLEIC ACID ANALYSIS

(75) Inventors: Robert J. Meagher, Mountain House, CA (US); Wyatt N Vreeland, Washington, DC (US); Annelise E. Barron, Palo Alto, CA (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 11/960,185

(22) Filed: Dec. 19, 2007

(65) Prior Publication Data

US 2008/0227211 A1    Sep. 18, 2008

Related U.S. Application Data

(60) Provisional application No. 60/875,635, filed on Dec. 19, 2006.

(51) Int. Cl.
*C12Q 1/68* (2006.01)
*C07H 21/04* (2006.01)

(52) U.S. Cl. .................................. 435/6.11; 536/24.33

(58) Field of Classification Search ........................ None
See application file for complete search history.

(56) References Cited

U.S. PATENT DOCUMENTS

| | | | |
|---|---|---|---|
| 5,171,534 | A | 12/1992 | Smith et al. |
| 5,332,666 | A | 7/1994 | Prober et al. |
| 5,567,292 | A | 10/1996 | Madabhushi et al. |
| 5,821,058 | A | 10/1998 | Smith et al. |
| 6,322,980 | B1 * | 11/2001 | Singh .................................. 435/6 |
| 6,358,385 | B1 | 3/2002 | Madabhushi et al. |
| 2003/0088056 | A1 * | 5/2003 | Barron ........................... 530/324 |
| 2006/0177840 | A1 * | 8/2006 | Slater et al. ........................ 435/6 |

FOREIGN PATENT DOCUMENTS

WO    9320236    10/1993

OTHER PUBLICATIONS

Vreeland et al. Multiplexed, High-Throughput Genotyping by Single-Base Extension and End-Labeled Free-Solution Electrophoresis. Analytical Chemistry (2002) 74(17): 4328-4333.*
Wacholder et al. Assessing the probability that a positive report is false: an approach for molecular epidemiology studies. Journal of the National Cancer Institute (2004) 96(6): 434-442.*
Lucentini et al. Gene association studies typically wrong. The Scientist (2004) vol. 18. 6 pages.*
Ioannidis et al. Replication validity of genetic association studies. Nature genetics (2001) 29:306-309.*
Listgarten et al. Predictive models for breast cancer susceptibility from multiple single nucleotide polymorphisms. Clinical Cancer Research (2004) 10: 2725-2737.*
Lee et al. Mutation in hepatocyte nuclear factor-1alpha is not a common cause of MODY and early-onset type 2 diabetes in Korea. Acta Diabetologica (2001) 38: 123-127.*
Rissanen et al. Variants in the hepatocyte nuclear factor-1alpha and -4alpha genes in Finnish and Chinese subjects with late-onset type 2 diabetes. Diabetes Care (2000) 23(10): 1533-1538.*
Meagher et al. Free-solution electrophoresis of DNA modified with drag-tags at both ends. Electrophoresis (2006) 27: 1702-1712.*
Meagher et al. End-labeled free-solution electrophoresis of DNA. Electrophoresis (2005) 26: 331-350.*
T.E. Creighton, "Amino Acid Residues," in Proteins, 2nd ed., New York: WH Freeman, 1993, pp. 8-13.*
Won et al. Protein polymer drag-tags for DNA separations by end-labeled free-solution electrophoresis. Electrophoresis (2005) 26: 2138-2148.*
Rachlin J. et al. "MuPlex: multi-objective multiplex PCR assay design." Nucleic Acids Research 2005, 33, W544-W547.
Kaderali L. et al. "Primer-design for multiplexed genotyping." Nucleic Acids Research 2003,31,1796-1802.
Meagher, Robert James, A Dissertation entitled "DNA Sequencing, Genotyping, and Analysis by End-Labeled Free-Solution Electrophoresis (ELFSE)"; publicly disclosed on Jan. 27, 2006.
Collins, F.S. et al. "A DNA polymorphism discovery resource for research on human genetic variation." Genome Research 1998, 8, 1229-1231.
Strittmatter, W.J. et al. "Apolipoprotein E and Alzheimer disease." Proceedings of the National Academy of Sciences of the United States of America 1995, 92, 4725-4727.
Greenblatt, M.S. et al. "Mutations in the p53 tumor suppressor gene: clues to cancer etiology and molecular pathogenesis." Cancer Research 1994, 54, 4855-4878.
Birch, J.M. et al. "Relative frequency and morphology of cancers in carriers of germline TP53 mutations." Oncogene 2001, 20, 4621-4628.
Olivier, M. et al. "Li-fraumeni and related syndromes: correlation between tumor type, family structure, and TP53 genotype." Cancer Research 2003, 63, 6643-6650.
Kirk, B.W. et al. "Single nucleotide polymorphism seeking long term association with complex disease." Nucleic Acids Research 2002, 30, 3295-3311.
Landegren, U. et al. "Reading bits of genetic information: methods for single-nucleotide polymorphism analysis." Genome Research 1998, 8, 769-776.
Chen, X. et al. "Single nucleotide polymorphism genotyping: biochemistry, protocol, cost and throughput." Pharmacogenomics Journal 2003, 3, 77-96.
Hirschhorn, J. N. et al. "SBE-TAGS: an array-based method for efficient single-nucleotide polymorphism genotyping." Proceedings of the National Academy of Sciences of the United States of America 2000,97, 12164-12169.
Pastinen, T. et al. "Multiplex, fluorescent, solid-phase minisequencing for efficient screening of DNA sequence variation." Clinical Chemistry 1996, 42, 1391-1397.
Pastinen, T. et al. "Minisequencing: a specific tool for DNA analysis and diagnostics on oligonucleotide arrays." Genome Research 1997, 7, 606-614.

(Continued)

*Primary Examiner* — Young J Kim
*Assistant Examiner* — Angela M Bertagna
(74) *Attorney, Agent, or Firm* — Casimir Jones, S.C.

(57) ABSTRACT

The present invention provides compositions and methods for performing free-solution conjugate analysis of nucleic acid molecules. For example, the present invention provides multiplexed single-base extension assays for genotyping. In particular, the present invention provides a series of disperse polyamide "drag tags" for use in achieving high-resolution separation of nucleic acid reaction products.

2 Claims, 11 Drawing Sheets

OTHER PUBLICATIONS

Sanger, F. et al. "DNA sequencing with chain-terminating inhibitors." Proceedings of the National Academy of Sciences of the United States of America 1977, 74, 5463-5467.

Vreeland, W. N. et al. Analytical Chemistry 2002, 74, 4328-4333.

Albarghouthi, M. N. et al. "Poly-N-hydroxyethylacrylamide (polyDuramide): A novel, hydrophilic, self-coating polymer matrix for DNA sequencing by capillary electrophoresis." Electrophoresis 2002, 23, 1429-1440.

Albarghouthi et al., "Poly-N-hydroxyethylacrylamide as a novel adsorbed coating for protein separation by capillary electrophoresis," Electrophoresis, 2003, 24:1166-1175.

Beck, S., "Colorimetric-Detected DNA Sequencing," Analytical Biochemistry, 1987, 1164:514-520.

Bell et al., "SNPstream UHT: Ultra-High Throughput SNP Genotyping for Pharmacogenomics and Drug Discovery," Biotechniques, 2002, 32:S70-S77.

Brookes, A. J., "The essence of SNPs," Gene, 1999, 234:177-186.

Chiesl et al., "Poly(acrylamide-co-alkylacrylamides) for Electrophoretic DNA Purification in Microchannels," Anal. Chem., 2005, 77:772-779.

Desruisseaux et al., "Electrophoresis of Composite Molecular Objects. 1. Relation between Friction, Charge, and Ionic Strength in Free Solution," Macromolecules, 2001, 34:44-52.

Ferrance et al., "Developments toward a complete micro-total analysis system for Duchenne muscular dystrophy diagnosis," Analytica Chimica Acta, 2003, 500:223-236.

Haynes et al., "Comblike, Monodisperse Polypeptide Drag-Tags for DNA Seprations by End-Labeled Free-Solution Electrophoresis (ELFSE)," Bioconjugate Chemistry, 2005, 16:929-938.

Heller et al., "Free-solution electrophoresis of DNA," J. Chromatography A, 1998, 806:113-121.

Hermanson, G. Bioconjugate Techniques, 1996, Academic Press, Inc: San Diego, CA, pp. 168-169 and 184-187.

Kim et al., "Thirtyfold multiplex genotyping of the p53 gene using solid phase capturable dideoxynucleotides and mass spectrometry," Genomics, 2004, 83:924-931.

Lilian et al., "A review of DNA sequencing techniques," Quart. Rev. of Biophys., 2002, 35:169-200.

Long et al., "Electrophoresis of polyampholytes," J. Chem. Phys., 1998, 108:1234-1244.

Makridakis et al., "Multiplex Automated Primer Extension Analysis: Simultaneous Genotyping of Several Polymorphisms," Biotechniques, 2001, 31:1374-1380.

Mayer et al., "Theory of DNA Sequencing Using Free-Solution Electrophoresis of Protein-DNA Complexes," Anal. Chem., 1994, 66:1777-1780.

McCormick et al., "Capillary electrophoretic separation of uncharged polymers using polyelectrolyte engines: Theoretical model," J. Chromatography A, 2001, 924:43-52.

McCormick et al., "The molecular end effect and its critical impact on the behavior of charged-uncharged polymer conjugates during free-solution electrophoresis," Electrophoresis, 2005, 26:1659-1667.

Nkodo et al., "Diffusion coefficient of DNA molecules during free solution electrophoresis," Electrophoresis, 2001, 22:2424-2432.

Noolandi, J., "A new concept for sequencing DNA by capillary electrophoresis," Electrophoresis, 1992, 13:394-395.

Paegel et al., "Microchip Bioprocessor for Integrated Nanovolume Sample Purification and DNA Sequencing," Anal. Chem., 2002, 74:5092-5098.

Paegel et al., "Microfluidic devices for DNA sequencing: sample preparation and electrophoretic analysis," Curr. Opin. Biotechnology, 2003, 14:42-50.

Ren et al., "Separating DNA sequencing fragments without a sieving matrix," Electrophoresis, 1999, 20:2501-2509.

Ross et al., "High level multiplex genotyping by MALDI-TOF mass spectrometry," Nature Biotechnology, 1998, 16:1347-1351.

Sanchez et al., "A multiplex assay with 52 single nucleotide polymorphisms for human identification," Electrophoresis, 2006, 27:1713-1724.

Shultz-Lockyear et al., "Effects of injector geometry and sample matrix on injection and sample loading in integrated capillary electrophoresis devices," Electrophoresis, 1999, 20:529-538.

Soussi et al., "Assessing TP53 status in human tumours to evaluate clinical outcome," Nature Reviews Cancer, 2001, 1:233-240.

Soussi et al., "p53 mutation heterogeneity in cancer," Biochem. Biophys. Res. Comm., 2005, 331:834-842.

Strittmatter et al., "Apolipoprotein E: High-avidity binding to Beta-amyloid and increased frequency of type 4 allele in late-onset familial Alzheimer disease," PNAS, 1993, 69:1977-1981.

Sudor et al., "End-Label, Free-Solution Capillary Electrophoresis of Highly Charged Oligosaccharides," Anal. Chem., 1995, 67:4205-4209.

Sudor et al., "End-Label, Free-Solution Capillary Electrophoresis of the Low Molecular Weight Heparins," Anal. Chem., 1997, 69:3199-3204.

Syvanen et al., "A Primer-Guided Nucleotide Incorporation Assay in the Genotyping of Apolipoprotein E," Genomics, 1990, 8:684-692.

Taylor et al., "The Classification of Amino Acid Conservation," J. Theor. Biol., 1986, 119(2):205-218.

Voet and Voet, Biochemistry, 2nd Ed., John Wiley & Sons, Inc. Table of Contents provided. Will provide specific pages upon Examiner request, published 1995.

Vreeland et al., "Molar Mass Profiling of Synthetic Polymers by Free-Solution Capillary Electrophoresis of DNA-Polymer Conjugates," Anal. Chem. 2001, 73:1795-1803.

Vreeland et al., "Multiplexed, High-Throughput Genotyping by Single-Base Extension and End-Labeled Free-Solution Electrophoresis," Anal. Chem., 2002, 74:4326-4333.

Won et al., "A New Cloning Method for the Preparation of Long Repetitive Polypeptides without a Sequence Requirement," Macromolecules, 2002, 35:8281-8287.

Won et al., Characterization of Glutamine Deamidation in a Long, Repetitive Protein Polymer via Bioconjugate Capillary Electrophoresis, Biomacromolecules, 2004, 5:618-627.

Zuckermann et al., "Efficient Method for the Preparation of Peptoids [Oligo(N-substituted glycines)] by Submonomer Solid-Phase Synthesis," J. Am. Chem. Soc., 1992, 114:10646-10647.

* cited by examiner

COMPOSITIONS AND METHODS FOR FREE-SOLUTION CONJUGATE NUCLEIC ACID ANALYSIS

The present application claims priority to U.S. Provisional Application 60/875,635 filed Dec. 19, 2006, which is herein incorporated by reference.

This invention was made with government support under Grant No. 5R01HG002918 awarded by the National Institutes of Health, the National Human Genome Research Institute. The government has certain rights in the invention.

FIELD OF THE INVENTION

The present invention provides compositions and methods for performing free-solution conjugate analysis of nucleic acid molecules. For example, the present invention provides multiplexed single-base extension assays for genotyping. In particular, the present invention provides a series of disperse polyamide "drag tags" for use in achieving high-resolution separation of nucleic acid reaction products.

BACKGROUND OF THE INVENTION

Although the sequencing of the first human genome was completed amidst much fanfare in 2003, a great need still exists for studying variability among different individual human genomes as well as among the genomes of other organisms. More than 90% of the genetic variability among humans is thought to consist of single-nucleotide polymorphisms (SNPs), and efforts are ongoing to map more than 300,000 SNPs.[1,2] While many SNPs have no significant impact on protein expression or cell function, specific SNPs have been found to predispose individuals to certain diseases, including sickle cell anemia and Alzheimer's disease.[3,4] For example, mutations in the p53 gene have been implicated in a wide variety of human cancers, with missense mutations comprising a large majority of deleterious p53 sequence alterations.[5-9] Furthermore, sequence polymorphisms in a variety of interacting genes are suspected to be responsible for complex diseases such as cancer, heart disease and psychiatric disorders; the results of multiplexed, multigene SNP analyses in large populations are expected to enable valuable insights into such conditions.[1,10]

A wide variety of techniques has been proposed for SNP detection, and many of these methods have recently been reviewed.[11,12] Most methods begin with PCR amplification of the gene region to be tested, typically followed by an enzymatic allele discrimination reaction, and then the detection and identification of the reaction products. Biomolecule detection schemes based on fluorescence or fluorescence resonance energy transfer, mass spectrometry, or microarrays can allow accurate identification of allele-specific products. Each method has its advantages and disadvantages with respect to simplicity, sensitivity, ease of multiplexing, throughput, and cost; the choice of SNP genotyping method varies depending on the specific needs and resources of each laboratory.

One widely used technique for allele discrimination based on the synthesis activity of DNA polymerase is the single-base extension (SBE) assay, also known as mini-sequencing or primer-guided nucleotide incorporation.[13-15] In this technique, an oligonucleotide primer is hybridized with its 3' end immediately upstream of the locus to be genotyped. The SBE reaction is analogous to Sanger cycle sequencing,[16] except that only chain terminators (ddNTPs) are included in the reaction. The DNA polymerase incorporates the ddNTP complementary to the target base on the template, and further extension of the DNA chain does not occur. A variety of different detection schemes can be used to determine the identity of the ddNTP that was incorporated and the genotype of the target allele. SBE followed by MALDI-TOF mass spectrometry,[17,18] solid-phase mediated fluorescence detection,[19] or electrophoresis with 4-color LIF detection[20] are all capable of multiplexed allele discrimination and detection.

Electrophoretic separation is an attractive method for separating SBE reaction products because capillary array electrophoresis (CAE) instruments are widely available; however, it tends to be a relatively costly approach to SNP detection,[12] in part because CAE instruments are expensive to purchase and maintain. Increased throughput, either by higher order multiplexing (more SNPs per capillary) or shorter analysis time, is required to make electrophoretic separation competitive for SNP detection. Both of these goals can be achieved by using free-solution conjugate electrophoresis (FSCE) in place of conventional electrophoresis with a gel or polymer sieving matrix. FSCE, which is sometimes called end-labeled free-solution electrophoresis (ELFSE),[21-24] is also expected to simplify the transition to microfluidic electrophoresis devices, which promise to be both faster and much less expensive than the bulky, complex CAE instruments, and to greatly expand the range of potential users of this technology.

What are needed are new tools and approaches for practicing FSCE so that its potential as a viable technology to aid in SNP detection is realized.

SUMMARY OF THE INVENTION

The present invention provides compositions and methods for performing free-solution conjugate analysis of nucleic acid molecules. For example, the present invention provides multiplexed single-base extension assays for genotyping. In particular, the present invention provides a series of disperse polyamide "drag tags" for use in achieving high-resolution separation of nucleic acid reaction products.

In one embodiment, the present invention provides compositions and methods comprising a bioconjugate approach in performing multiplexed single-base extension (SBE) assays. For example, the compositions of the present invention are demonstrated herein to be useful in genotyping a large panel of point mutants in exons 5-9 of the p53 gene. However, the present invention is not limited to the point mutation being genotyped, and it is contemplated that a multitude of genetic mutations can be genotyped by applying the compositions and methods as described herein.

The "drag-tag", a synthetic, uncharged, unlabeled polyamide of precise length, modifies the electrophoretic mobility of the DNA, allowing for rapid electrophoretic separation, facilitating peak identification. In one embodiment, a series of monodisperse polyamide drag-tags was developed using both chemical and biological synthesis. In some embodiments, the drag-tags find utility in achieving high-resolution separation of genotyping reaction products by microchannel electrophoresis without a polymeric sieving matrix. For example, a highly multiplexed SBE reaction was performed in which 16 unique drag-tagged primers were used simultaneously to probe 16 different p53 gene loci, with an abbreviated thermal cycling protocol of only 9 minutes. The drag-tagged SBE products were separated by free-solution conjugate electrophoresis (FSCE) in both capillaries and microfluidic chips with genotyping accuracy in excess of, for example, 96%. In the example, the separation required less than 70 seconds in a glass microfluidic chip, or about 20 minutes in a commercial capillary array sequencing instrument. Therefore, it is contemplated that compared to gel electrophoresis, FSCE offers greater freedom in the design of SBE primers by essentially decoupling the length of the primer and the electrophoretic mobility of the genotyping products. In some embodiments, FSCE in combination with the compositions of the present invention provides the facile implementation of SBE on integrated microfluidic electrophoresis devices for rapid, high-throughput genetic mutation detection or SNP scoring.

The compositions and methods of the present invention are not limited to use in SNP detection or multiplex genotype analysis. A wide variety of nucleic acid analysis and characterization techniques may employs the compositions and methods of the present invention. Exemplary methods are described herein, although the present invention is not limited to these examples.

DETAILED DESCRIPTION OF THE INVENTION

The following description provides exemplary embodiments of the present invention. The present invention is not limited to these exemplary embodiments.

Figure 1:
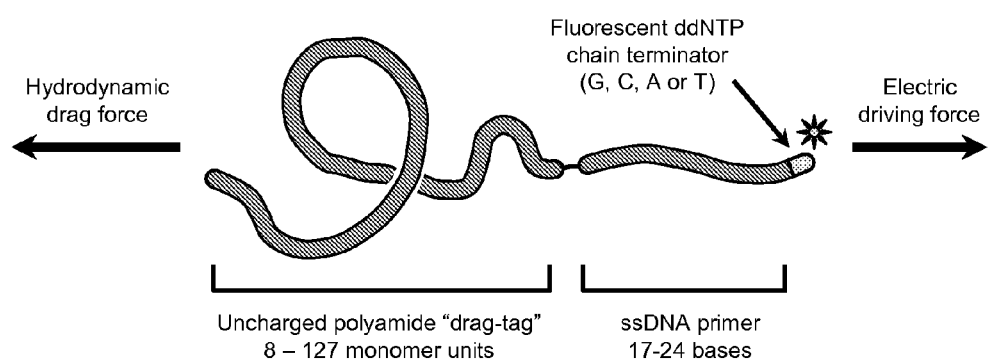
FIG. 1 is an exemplary schematic representation of a DNA-drag-tag conjugate. The DNA primer is designed to probe the template locus of interest by adding one dideoxynucleotide with an identifying fluorophore and ranges in size from 17 to 23 bases. The drag-tag, a synthetic, uncharged, unlabeled polyamide of precise length, modifies the electrophoretic mobility of the DNA, allowing for rapid electrophoretic separation, facilitating peak identification.

FSCE is a bioconjugate technique for separating charged biopolymers by microchannel electrophoresis in the absence of a gel or sieving matrix. It is contemplated that monodisperse, uncharged polyamide "drag-tags" are appended to one or both ends of a collection of polydisperse, negatively charged nucleic acid molecules (e.g. DNA) to create nucleic acid-polyamide bioconjugates that have size-dependent free-solution electrophoretic mobilities (FIG. 1). For a given bioconjugate, the mobility is determined by both the size of the DNA "engine" (which experiences both an electrophoretic force and hydrodynamic drag force proportional to DNA size in an applied electric field), and by the hydrodynamic friction added by the drag-tag, which is proportional to drag-tag molar mass.[24-28] The approach was demonstrated for the size-based separation of DNA sequencing fragments up to 110 bases in length,[23] denatured single-stranded PCR products,[29,30] and double-stranded DNA restriction fragments,[22] as well as profiling of heparins[31] and charged oligosaccharides.[32] The exemplary studies used capillary electrophoresis (CE) in free solution, i.e., without a gel or sieving matrix of any kind.

FSCE separation of the products of a 3-fold multiplexed SBE reaction by free-solution CE were previously demonstrated.[33] Using conventional SBE reaction protocols, 3 different oligonucleotide primers were used to interrogate 3 polymorphic loci in p53 exon 8. Each primer was conjugated to a monodisperse, synthetic polyamide drag-tag of unique length, allowing the SBE products to be separated by free-solution electrophoresis. Electrophoretic separation was performed in a MegaBACE CAE instrument; although the peaks were somewhat broad, there was sufficient resolution to allow accurate genotyping of each locus in several mutant samples.

In one embodiment, the compositions and methods of the present invention provide a SBE-FSCE technique that achieves a higher degree of multiplexing (e.g., 4 or more, 5 or more, 6, 7, 8, 9, 10, 11, 12, 13, 15, 16, 20, etc.), exemplified herein using 16 different oligonucleotide primers and 16 unique drag-tags to simultaneously genotype 16-p53 loci. In some embodiments, an abbreviated thermal cycling protocol cuts down the reaction time, and DNA-drag-tag peak resolution is greatly improved. For example, numerous p53 samples with previously characterized point mutations in exons 5-9 were analyzed and separated by both capillary and microfluidic chip electrophoresis. It is contemplated that a further increase in separation is accomplished by the creation of a wider array of unique drag-tags. By contrast, multiplexed SBE genotyping by gel electrophoresis requires the solid-phase synthesis and purification of DNA primers with long non-hybridizing "tails" to enable good electrophoretic separations in gels,[34] which rapidly becomes difficult as the tail length increases. In one embodiment, SBE-FSCE offers an added degree of flexibility over conventional SBE with easily interchangeable primers and drag-tags, offering many different types of multiplexed assays with a single set of drag-tags.

In one embodiment, the present invention provides a synthetic, uncharged monodisperse polyamide for modifying the electrophoretic mobility of DNA. In some embodiments, the uncharged monodisperse polyamide is appended to one end of a DNA molecule. In some embodiments, the uncharged monodisperse polyamide is appended to both ends of a DNA molecule. In some embodiments, the bioconjugates of DNA-polyamides and DNA exhibit size dependent free-solution electrophoretic mobility. In some embodiments, the bioconjugates of DNA-polyamides are used in detection of single nucleotide polymorphisms. In some embodiments, the bioconjugates of DNA-polyamides are used to detect and diagnose disease states, for example cancers, cystic fibrosis, muscular dystrophy, Alzheimer's disease, diabetes, sickle cell anemia. In some embodiments, the bioconjugates of DNA-polyamides are used to detect a subject with a genetic predisposition to a disease state. In some embodiments, the bioconjugates of DNA-polyamides are used to analyze a subject's SNP profile for drug therapy efficacy and potential design of useful therapeutics for a particular individual based on the SNP profile (e.g., personalized medicine).

In one embodiment, the bioconjugates of DNA-polyamides find utility in electrophoretic methods such as capillary electrophoresis using a free-solution matrix instead of a gel matrix. In some embodiments, the bioconjugates are used in methods for SNP detection by free solution conjugate electrophoresis. In some embodiments, the compositions and methods of the present invention as described herein are used for multiplex SNP detection.

The present invention includes kits and compositions for conducting methods of the invention. For example, kit or compositions (e.g., reaction mixtures) may include sets of primers conjugated to a plurality of different drag-tags, reagents for making such primers, dyes, detection components, polymerase, buffers, control reagents, or other components useful, necessary, or sufficient for conducting the methods.

Compositions and methods of the present invention may also be used in the context of nucleic acid sequencing reactions. For example, the present invention provides systems, compositions, and methods for nucleic acid sequencing in free-solution using protein polymer drag-tags. As such, the present invention provides protein-based molecular compositions that find use as drag-tags for use in sequencing methods and provides systems and methods for automated sequencing of nucleic acids in free-solution electrophoresis.

In particular, the present invention demonstrates for the first time the separation of sequencing fragments by free-solution conjugate electrophoresis (FSCE) using a non-natural, genetically engineered protein polymer drag-tag, with significantly higher resolution and cleaner results than previously reported for this sequencing technique. FSCE is an approach for size-based separation of DNA in the absence of a sieving matrix, which is enabled by the end-on attachment of a polymeric "drag-tag" that modifies the charge-to-friction ratio of nucleic acid fragments in a size-dependent fashion. Progress in FSCE separations has previously been limited by the lack of suitable large, monodisperse drag-tags, but this hurdle has been overcome by the present invention. For example, the present invention provides compositions designed (e.g., de novo) that are non-natural, unfolded (or "random-coil"), genetically engineered, amino acid protein polymers useful as an FSCE drag-tag. The resulting separation is essentially diffusion limited, without significant adsorption of the drag-tag to capillary walls. These compositions find use for very rapid separations without the difficulties associated with sieving polymers. As such, the compositions, system, and methods of the present invention permit faster, more efficient, and more cost-effective routes for high-throughput sequencing and other nucleic acid analysis techniques that require high resolution separation of nucleic acid molecules as a function of size.

Experiments conducted during the development of the present invention employed the production of long, repetitive polypeptides or "protein polymers" (J. I. Won, R. J. Meagher, A. E. Barron, *Electrophoresis* 26, 2138 (2005)). Using techniques of genetic engineering, artificial genes are constructed that encode for polypeptides with simple repetitive sequences (J. I. Won, A. E. Barron, *Macromolecules* 35, 8281 (2002)). Work described in J. I. Won, R. J. Meagher, A. E. Barron, *Electrophoresis* 26, 2138 (2005) and J. I. Won, R. J. Meagher, A. E. Barron, *Biomacromolecules* 5, 618 (March-April, 2004) discusses some initial attempts to create protein polymer drag-tags for FSCE, which ultimately were not useful because of sub-optimal choice of the amino acid sequences.

Further experiments conducted during the development of the present invention overcame these initial difficulties and provided protein polymer drag-tags having the desired properties. For example, a new protein polymer sequence based on modifications to the sequences discussed in references cited above was generated. The new protein polymer sequence contained repeats of the amino acid sequence (Gly-Ala-Gly-Thr-Gly-Ser-Ala (SEQ ID NO:1)), which differs from the sequence in Won et al., 2005 in the replacement of the unstable glutamine by the stable, hydrophilic threonine residue. A controlled cloning technique (J. I. Won, A. E. Barron, *Macromolecules* 35, 8281 (2002)) was used to create multimers of the artificial gene encoding for this sequence, ultimately expressing a protein polymer with 18 repeats of the sequence (a total of 127 amino acids). This protein polymer, although small, was tested for sequencing, with excellent results that surpassed the original sequencing study performed with streptavidin in 1999 (Ren et al., supra). The present invention contemplates the use of these and related (e.g., larger) protein polymers to permit free-solution sequencing of nucleic acid fragments having a variety of sizes. The description provided herein describes parameters of protein polymer (or mimetics thereof) that find use in the systems and methods of the present invention.

In some embodiments, the present invention provides methods for nucleic acid sequencing, comprising the steps of: providing nucleic acid fragments generated in a nucleic acid sequencing reaction from a target nucleic acid to be sequenced (e.g., generating nucleic acid fragments in a sequencing reaction); separating the nucleic acid fragments (e.g., that are conjugated to drag-tags) in free-solution (e.g., by free-solution microchannel electrophoresis) containing synthetic polymer drag-tags; and identifying a sequence of the target nucleic acid by analyzing the separated nucleic acid fragments. The nucleic acid fragments may be generated by any sequencing method. In some embodiments, the fragments are generated in a Sanger sequencing method. In some embodiments, the fragments are generated in a cycle sequencing method. In some embodiments, the fragments are contained in a population of molecules that provide a sequencing ladder, such that the fragments differ from one another in single-nucleotide increments. The present invention is not limited by the size of the fragments generated or analyzed, nor by the specific enzymatic or chemical reaction utilized to produce the drag-tagged DNA molecules to be sequenced. In some embodiments, however, the fragments include at least some that are greater than 120 bases in length (e.g., at least 150 basedbases, 180 bases, etc.).

The present invention is not limited by the manner in which the drag-tags are utilized in the free-solution method to separate fragments. However, in some embodiments, the drag-tags are covalently attached to the nucleic acid fragments. While they may be attached after the initial generation of the fragments, in some embodiments, the fragments are generated containing the drag-tags through the use of sequencing primers that are coupled to the drag-tags. However, the present invention is not limited by the method by which the drag-tags are conjugated to the DNA primers or DNA sequencing fragments.

The methods may be conducted in any setting. However, in some preferred embodiments, fragments are separated and analyzed in capillary tubes. This permits the methods to be used in the context of existing automated sequencing devices wherein the free solution capillary tubes of the invention are substituted for the gel containing tubes of the prior systems and devices. The methods may also be conducted on solid surfaces, such as on cards or chips containing microchannels. It is contemplated that such cards or microfluidic chips may, for example, be fabricated from any sort of glass, plastic, or elastomer material. Any of these systems may employ the appropriate detectors to collect data and appropriate software to analyze and report results from the data.

The present invention is not limited by the nature of the synthetic protein-based polymer drag-tag. In some embodiments, the protein polymer drag-tag is configured such that, in use, it is in an unfolded form. In some embodiments, the drag-tag preparation used is substantially homogenous (e.g., greater than 90%, 95%, 99%, or all detectable levels, possess the same chemical structure). In some embodiments, the drag-tag is selected such that it does not significantly (e.g., no detectable loss in signal or results) adsorb to a glass or plastic wall of a reaction vessel (e.g., a capillary tube). Chemically engineered mimetics of polypeptide sequences may also be employed. In some embodiments, the protein polymer comprises a repeating amino acid sequence. For example, a repeated sequence of 5-10 amino acids used to generate a polymer containing a desired number of repeats (e.g., 10, 11, 12, 13, 14, . . . , 18, . . . , 20, . . . 24, . . . , etc.) to generate an appropriately sized drag-tag. In some embodiments, a plurality (i.e., 2 or more) of the same or different repeated sequences are conjugated to a scaffold to generate larger complexes. Any type of scaffold may be used including, but not limited to, dendrimers or other organic or inorganic molecules or assemblies that provide multiple attachment sites for conjugation to the peptide sequences. In some embodiments, the drag-tag comprises a plurality of the motif Gly-Ala-Gly-Thr-Gly-Ser-Ala or functional equivalents thereof.

The present invention contemplates variations of the sequence comprising conserved or non-conserved amino acid substitutions at one or more (e.g., 2, 3, 4, . . . etc.) positions in each repeat unit or one or more positions in a subset of the repeat units in the polymer. In some embodiments, at least 60% (e.g., 65%, 75%, 80%, 90%, 95%, etc.) of the amino acids in the polymer are not substituted. For example, as used herein Gly (glycine), Ala (alanine), Ser (serine) and Thr (threonine) are known as relatively polar or hydrophilic, uncharged amino acids, as are Asn (asparagine), Trp (tryptophan), and Gln (glutamine). A plurality of these amino acids, with the greatest number of amino acids being chosen from among Gly, Ala, Ser, and Thr, can be chosen to create a protein that is water-soluble and that will tend to have a predominantly unfolded (random-coil) structure in aqueous solution. In some embodiments, sparing use can be made of negatively charged amino acids such as Asp (aspartate), and Glu (glutamate) to increase water-solubility. Further, Leucine (Leu) is a relatively hydrophobic amino acid as are Phe (phenylalanine), Ile (isoleucine), Pro (proline) and Val (valine). It is contemplated that these amino acids can be used, but more sparingly than the relatively hydrophilic amino acids defined above. In some embodiments, certain sulfur-containing amino acids such as Cys (cysteine) and Met (methionine) can be used in very small amounts if at all, since they are chemically reactive (Voet and Voet, *Biochemistry*, $2^{nd}$ Ed., John Wiley & Sons, Inc. pp. 1361). Additional functionally equivalent properties of amino acids are described, for example, in Taylor, J. Theor. Biol. 119(2):205-18 (1986) (incorporated herein in its entirety), where a Venn diagram of the relationship between the 20 amino acids is depicted using the parameters of size, aliphatic and aromatic properties, hydrophobicity, charge and polarity. It is contemplated that any of the amino acids demonstrating similar functional properties are interchangeable in generating a polymer of the present invention.

Motifs may be joined end-to-end or may be separated by spacers, including additional amino acid sequences.

The present invention also provides kits for carrying the methods described herein. For example, for sequencing methods employing di-deoxy nucleotides, the kit may comprise: a) a synthetic protein-based polymer drag-tag; and b) one or more dideoxy nucleotides. The kits may also include any one or more components useful, necessary, or sufficient for carrying the various methods, including, but not limited to, a polymerase, a polymerase dilution buffer, a dithiothreitol-containing solution, an aqueous buffer containing a divalent cation, positive control target nucleic acid, control primer, stop solution, and instructions. In some embodiments, the kit comprises the drag-tag covalently coupled to a primer.

The present invention likewise provides various compositions (e.g., reaction mixtures, devices, etc.) used in the methods. For example, the present invention provides compositions comprising a nucleic acid molecule containing a synthetic protein-based polymer drag-tag and a dideoxy nucleotide. The present invention also provides a composition comprising a primer conjugated to a synthetic protein polymer drag-tag.

The drag-tags of the present invention offer a new class of molecules that enable application of free-solution conjugate electrophoresis technologies that were not prior available. The experimental example and description provide herein describes desirable characteristics of drag-tags and means for assessing drag-tag performance and properties. While certain structure of exemplary drag-tags are provided herein, it should be understood that other structure having the desired functions and properties are within the scope of the invention. One or more different drag-tags (e.g., different sizes) of the invention may be used alone or together in a variety of nucleic acid analysis methods to assist in the characterization of nucleic acids.

The experimental examples, below, demonstrate certain methods of the invention by employing drag-tags having a repeating sequence motif of Gly-Ala-Gly-Thr-Gly-Ser-Ala and variations thereof. In some preferred embodiments, drag tags comprising this sequence are used. The present invention contemplates variations of this motif as well. For example, any rearranged sequence of these amino acids is contemplated for use as a drag-tag. Guidance for considering the properties of the individual amino acids for generating alternate protein sequences that find use for FSCE applications, are discussed above. The biochemical properties of the 20 common amino acids are well characterized (Voet and Voet, Biochemistry, 2$^{nd}$ Ed., John Wiley & Sons, Inc. pp. 1361). Gly (glycine), Ala (alanine), Ser (serine), Thr (threonine) and Trp (tryptophan) are considered relatively polar, uncharged amino acids, which are also relatively chemically stable, and can be considered to be the most desirable amino acids for use in a protein-based drag-tag, and should predominate in the sequence (e.g., greater than 50%, greater than 60%, greater than 70%, 80%, 90%, etc. of the amino acids in the polymer are from this group). Other polar amino acids, which are somewhat less chemically stable, are Asn (asparagine) and Gln (glutamine). A plurality of these amino acids, with the greatest number of amino acids being chosen from among Gly, Ala, Ser, and Thr, can be chosen to create a protein that is water-soluble (as needed for FSCE) and contemplated to have a predominantly unfolded (random-coil) structure in aqueous solution, which maximizes the drag provided by the protein polymer. More sparing use of the amino acids Gln and Asn should be made, since these amino acid side-chains can spontaneously undergo a biochemical reaction such that they deamidate in aqueous solution over time, to produce Glu and Asp side chains, which are negatively charged and will affect the electrophoretic mobility of the drag-tag, ultimately contributing to heterogeneity. In the protein sequence design, an initial, sparing use of negatively charged amino acids such as Asp (aspartate), and Glu (glutamate) can be made to increase water-solubility; but too many of these negatively charged amino acids will decrease the effectiveness of the drag-tag to enable the separation of larger DNA fragments. The positively charged amino acids, Lysine (Lys) and Arginine (Arg), can also be used, and may be advantageous as they provide for the drag-tag to have an intrinsic electrophoretic mobility opposite to that of DNA molecules, which enhances the resistance to DNA migration in an electric field. However, too much use of positively charged amino acids could create non-ideal designs, since cationic drag-tags may complex strongly with DNA molecules or the fused silica or plastic capillary walls, which carry negative charge as commonly used. Therefore, a sparing use of such positively charged amino acids should be made, if they are used at all. If the amino terminus of the protein polymer is being used for the conjugation of the drag-tag to the DNA molecules, it may be desirable not to use the amino acid Lys, which has a primary amino group very similar to the amino terminus of the protein. Further, Leucine (Leu) can be defined as a relatively hydrophobic amino acid as are Phe (phenylalanine), Ile (isoleucine), Pro (proline) and Val (valine). These amino acids can be used, but should be employed more sparingly than the relatively hydrophilic amino acids defined above. The sulfur-containing amino acids such as Cys (cysteine) and Met (methionine) should be used in very small amounts if at all, since they are chemically reactive and hence could contribute to drag-tag sample heterogeneity. Additional functionally equivalent properties of amino acids are described, for example, in Taylor, J. Theor. Biol. 119(2):205-18 (1986) (incorporated herein in its entirety), where a Venn diagram of the relationship between the 20 amino acids is depicted using the parameters of size, aliphatic and aromatic properties, hydrophobicity, charge and polarity. It is contemplated that any of the amino acids demonstrating similar functional properties are interchangeable in generating a polymer of the present invention. Moreover, it is contemplated that a variety of non-natural amino acids or other organic chemical moieties could be introduced into a protein, using either enzymatic or organic chemical reaction methods, which also find use for the preparation of drag-tags for FSCE applications. Such non-natural amino acids, whether incorporated at the termini or the internal sequence of the protein, can be used to enhance the properties of the protein, for example to enhance its water solubility, or to enable facile conjugation of the drag-tag to DNA molecules.

Drag tags that find use in the compositions and methods of the present invention (e.g., sequencing compositions and methods) may have one or more of the following desired properties: they should be water-soluble under the conditions in which they are employed for conjugating DNA to them, as well as (preferably) the conditions of the DNA sequencing reaction and of the electrophoretic separation; they should provide a unique chemical functionality that allows them to be conjugated to DNA molecules, either end-on or at some other well-defined position in the DNA molecules, either before or after the sequencing reaction; they should not be chemically reactive nor tend to undergo spontaneous and uncontrolled degradation, multimerization, or aggregation under conditions in which they are commonly used or stored; they should not have a strong tendency to spontaneously adsorb to the internal surfaces of the analysis devices, nor to be strongly ionically attracted to DNA molecules under commonly encountered solution conditions; they should be amenable to essentially complete purification, such that a predominantly homogeneous preparation of the drag-tags may be prepared, and they should remain water-soluble under so-called "denaturing" conditions, which might include, for example, high temperatures and/or the use of chaotropic solution additives including urea, formamide and other small organic molecules used as denaturants, and a dimethylsulfoxide co-solvent. In some embodiments, the sequences are chosen such that that they can be produced in relatively high yields by a genetically engineered biological organism such as E. Coli, at least 10 mg/L of culturing medium, which may mean that the sequence should not be too simple, that is, that at least three different amino acids (of the common twenty amino acids found in nature) should be used. In some embodiments, the organism used to produce the protein should be able to produce it in relatively long lengths, preferably greater than 75 amino acids, and more preferably greater than 125 amino acids in length.

Compositions and methods of the invention find use in a variety of nucleic acid analysis methods and may be used as part of a system with a variety of existing devices, software components, and other analysis components.

The present invention also provides kits for carrying the methods described herein. For example, for sequencing methods employing di-deoxy nucleotides, the kit may comprise: a) a synthetic protein-based polymer drag-tag; and b) one or more dideoxy nucleotides. The kits may also include any one or more components useful, necessary, or sufficient for carrying the various methods, including, but not limited to, a polymerase, a polymerase dilution buffer, dithiothreitol solution, buffer containing a divalent cation, positive control target nucleic acid, control primer, stop solution, and instructions. In some embodiments, the kit comprises the drag-tag covalently coupled to a primer.

The present invention likewise provides various compositions (e.g., reaction mixtures, devices, etc.) used in the methods. For example, the present invention provides compositions comprising a nucleic acid molecule containing a synthetic protein-based polymer drag-tag and a dideoxy nucleotide or a dye-deoxy nucleotide. The present invention also provides a composition comprising a primer conjugated to a synthetic protein polymer drag-tag. The present invention also provides compositions for use in conjunction with U.S. Pat. No. 6,200,748 (incorporated herein in its entirety), where primers are labeled for use in sequencing reactions. The primers of the patent are coupled to either a chromophore or a fluorophore prior to use in a sequencing reaction, and the synthetic protein-based polymer drag-tag can additionally be complexed with such a molecule for improving upon the methods as described in the patent.

Compositions and methods of the present invention find utility with multiple CE nucleic acid analysis platforms, such as automated sequencing devices and systems. For example, ABI and Applied Biosystems market a number of fluorescent CE nucleic acid genetic analyzers such as ABI PRISM® 310 Genetic Analyzer, ABI PRISM® 3100 Genetic Analyzer, ABI® PRISM 3100-Avant™ Genetic Analyzer, Applied Biosystems 3130/3130xl Genetic Analyzers, and Applied Biosystems 3730/3730xl Genetic Analyzers. Other companies also make relevant instruments for capillary or microfluidic chip electrophoresis, including Agilent Inc. and Beckman-Coulter Inc. The ABI PRISM® 310 Genetic Analyzer has only one capillary tube chosen from two lengths, either 47 or 61 cm, and will accommodate 48 or 96 sample tubes. The ABI PRISM® 3100 and ABI® PRISM 3100-Avant™ Genetic Analyzers are DNA analysis systems with 16 or 4 capillary tubes, respectively, operating in parallel. Capillary tubes for the two systems come in 4 lengths, 22, 36, 50 and 80 cm long, with the run times increasing from around 20 minutes for the shorter tubes to over three hours for the 80 cm tubes. The Applied Biosystems 3130/3130xl Genetic Analyzers have 4 and 16 capillary tubes, respectively, with capillary length options the same as for the ABI PRISM® 3100, and can further accommodate 96 and 384 microtiter sample plates instead of sample tubes. The Applied Biosystems 3730/3730xl Genetic Analyzers contain either 48 or 96 capillary tubes, respectively, and use the same microtiter sample plate configuration as the 3130/3130xl instruments. The instruments as previously discussed are suitable for use with one or both dye-deoxy terminator dye systems (e.g., BigDye® and dRhodamine), however the present invention can be used with both terminator dye systems. Software accompanies each instrument for sample analysis and data interpretation, such as SeqScape®, GeneMapper®, and other Sequence Analysis software and defined by the instrument used. The fluorescence based CE systems of ABI and Applied Biosystems can perform multiple genetic analyses, including multiplex SNP genotype analysis (SNPlex, SnaPshot®), linkage mapping, restriction fragment length (RFLP) analysis, sequencing and Genetic Identity testing (e.g., DNA fingerprinting).

The aforementioned instruments marketed by ABI and Applied Biosystems are described in U.S. Pat. Nos. 6,358, 385, 5,821,058, 5,567,292, 5,332,666 and 5,171,534 (and foreign counterparts), incorporated herein in their entireties. Additional fluorescence based nucleic acids sequencing systems include, but are not limited to, CEQ™ 8000 Genetic Analysis System (Beckman Coulter) and 4300 DNA Analysis System by LI-COR.

However, the present invention is not limited to fluorescence based genetic analysis systems. It is contemplated that the compositions and methods of the present invention can be used in all types sequencing systems. For example, it is contemplated that other fluorimetric and non-fluorimetric nucleic acid sequencing systems can be used with the present invention, such as Pyrosequencing™ (e.g., real time sequencing by enzymatic cleavage of fluorescently labeled DNA), and non-fluorimetric Sanger enzymatic sequencing and Maxim & Gilbert sequencing other related chemical sequencing methods (Lilian et al., Quart. Rev. of Biophys. 35:169-200 (2002), incorporated herein in its entirety), and colorimetric DNA sequencing as described in Beck, Anal. Biochem. 164:514-20 (1987).

The following examples are provided in order to demonstrate and further illustrate certain preferred embodiments and aspects of the present invention and are not to be construed as limiting the scope thereof.

EXAMPLES

Example 1

—Synthesis of Polypeptoid Drag-Tags

A series of 14 linear polypeptoid drag-tags ranging in size from 8 to 60 N-methoxyethylglycine (NMEG) monomers was synthesized on an ABI 433A automated peptide synthesizer (Applied Biosystems, Foster City, Calif.) using the sub-monomer protocol.[28, 35] Aliquots of resin were removed every 4 cycles of peptoid synthesis beginning with the 8th cycle. Peptoid chains were capped at the N-terminus with 3-maleimidopropionic acid using diisopropylcarbodiimide (DIC) as a coupling reagent.[28] The maleimide-activated polypeptoids were cleaved from the resin with TFA and purified to near-total monodispersity by C18 reversed-phase HPLC. The monodispersity was assessed by FSCE by conjugating each polypeptoid to a fluorescently labeled, thiolated 20-base oligonucleotide, and analyzing by CE in free solution.[28]

The 15th drag-tag was a branched polypeptoid, consisting of a 30mer poly(NMEG) backbone derivatized with five 8mer oligo (NMEG) branches, activated at the N-terminus with sulfosuccinimidyl 4-(N-maleimidomethyl)-1-cyclohexane carboxylate (Sulfo-SMCC).[30] The 16th drag-tag was a linear protein polymer with the highly repetetive sequence (GAGTGSA)$_4$-GAGTGRA-(GAGTGSA)$_7$-GAGTGRA-(GAGTGSA)$_5$-G (SEQ ID NO:2), with a total length of 127 amino acids. An artificial gene encoding this protein polymer was constructed by the controlled cloning method,[29, 36, 37] and the protein polymer was expressed in *E. Coli*. Following purification by affinity chromatography, the protein polymer was activated at the N-terminus with Sulfo-SMCC to yield a maleimide-activated drag-tag.

Example 2

—Primers for Single-Base Extension Reactions

A set of 16 oligonucleotide primers, as shown in Table 1, was synthesized by Integrated DNA Technologies (Coralville, Iowa, USA). The primers range in length from 17 to 23 bases and include a 5'-thiol functionality to enable conjugation to maleimide-activated drag-tags. Each primer has a calculated $T_m$ of 55° C.±1° C. and was designed to avoid stable hairpin structures or extendable homodimers. The forward (+) and reverse (−) strands of p53 were both considered for primer design, especially when probing for mutations at 2 adjacent loci.

TABLE 1

| Exon | Locus | Strand | Sequence/SEQ ID NO | Drag-tag Size | Migration order | Wild Type |
|---|---|---|---|---|---|---|
| 9 | 328-1 | − | AAGACTTAGTACCTGAAGGGTGA (3) | 8 | 1 | A |
| 5 | 128-1 | + | CCTTCCTCTTCCTACAGTACTCC (4) | 12 | 2 | C |
| 9 | 330-2 | − | GGTCCCAAGACTTAGTACCTGA (5) | 16 | 3 | A |
| 6 | 198-1 | − | ACT CCA CAC GCA AAT TTC CTT (6) | 20 | 4 | C |
| 6 | 196-2 | − | ACA CGC AAA TTT CCT TCC ACT (7) | 24 | 5 | C |
| 7 | 249-3 | − | GTG ATG ATG GTG AGG ATG GG (8) | 28 | 6 | C |
| 6 | 196-1 | + | CCC CTC CTC AGC ATC TTA TC (9) | 32 | 7 | C |
| 7 | 245-1 | + | TAA CAG TTC CTG CAT GGG C (10) | 36 | 8 | G |
| 8 | 273-1 | + | ACG GAA CAG CTT TGA GGT G (11) | 40 | 9 | C |
| 8 | 273-2 | − | CCA GGA CAG GCA CAA ACA (12) | 44 | 10 | C |
| 5 | 173-1 | + | CAG CAC ATG ACG GAG GTT (13) | 48 | 11 | G |
| 6 | 221-3 | + | TGT GGT GGT GCC CTA TGA (14) | 52 | 12 | G |
| 5 | 149-1 | + | GTG CAG CTG TGG GTT GAT (15) | 56 | 13 | T |
| 5 | 175-2 | + | GAC GGA GGT TGT GAG GC (16) | 60 | 14 | G |
| 5 | 144-1 | + | CCA AGA CCT GCC CTG TG (17) | 70* | 15 | C |
| 5 | 173-2 | + | AGC ACA TGA CGG AGG TTI (18) | 127** | 16 | T |

Table 1 contains the primer designs for multiplexed SBE-FSCE. The drag-tags are all linear poly-N-methoxyethylglycines made by solid-phase synthetic methods, except for a branched 70mer NMEG (*)[30] and a linear 127mer genetically engineered protein polymer (**).

The 16 drag-tag-primer conjugates were created by reacting each thiolated primer with a different maleimide-activated drag-tag. The thiolated primers were reduced prior to conjugation by incubating 2 nmol of primer with a 20:1 molar excess of TCEP (Acros Organics, Morris Plains, N.J.) for 90 min at 40° C. Reduced DNA was conjugated to the drag-tags by mixing 90 pmol of reduced DNA with 2.5 nmol of drag-tag in a total volume of 10 μL of pH 7.2 sodium phosphate buffer. The DNA-drag-tag mixture was left to react at room temperature overnight. The large excess of drag-tag relative to DNA ensured nearly complete conjugation of DNA. As shown in Table 1, the DNA primers were conjugated to drag-tags in reverse order of length; the longest DNA primers were paired with the shortest drag-tags to ensure an unambiguous migration order of the conjugates during free-solution electrophoresis. The 16 drag-tag-primer conjugates were pooled prior to the multiplexed SBE reactions, with a total primer concentration of 2 pmol/μL.

Example 3

—Template DNA for SBE Reactions and SBE Reactions

Previously characterized p53 wild-type and mutant samples were a gift from the National Institute of Standards and Technology. Exons 5-9 of the p53 gene (including introns) were present as an insert of approximately 2 kbp in a plasmid cloning vector. A plasmid containing the wild-type p53 gene was available in large quantity, and was used directly as a template for SBE reactions. Plasmid DNA containing variants of p53 exons 5-9 with point mutations were available in much lower quantities; the entire 2 kbp insert covering exons 5-9 was PCR-amplified prior to the SBE reaction, a common first step in SNP detection.[12] Residual nucleotides and PCR primers that could interfere with the subsequent SBE reaction were digested by treating the PCR product with Shrimp Alkaline Phosphatase (USB, Cleveland, Ohio, USA) and Exonuclease I (USB) at 37° C. for 1 hour, followed by deactivation of the enzymes at 75° C. for 15 minutes.

SBE reactions were carried out using the SNaPshot Multiplex kit (Applied Biosystems, Foster City, Calif., USA), which includes a premix of sequencing polymerase, buffer concentrate, and ddNTP chain terminators labeled with 4 different dichlororhodamine (dRhodamine) dyes. The SBE reactions were prepared by mixing 2.5 μL of the SNaPshot premix, 0.5 μL of the pooled drag-tag primer mix (1 pmol total primer), 0.025-0.10 pmol of template DNA, 0.5 μL of 125 mM HCl and water for a total volume to 5 μL. The SBE reaction was carried out in 5 cycles: 96° C. for 2 sec (denaturation), 51.5° C. for 5 sec (annealing), and 60° C. for 10 sec (extension). The complete thermal cycling procedure required approximately 9 minutes. Excess dye terminators and buffer salts were removed using Centri-Sep gel filtration spin columns (Princeton Separations, Princeton, N.J., USA).

Example 4

—Capillary Electrophoresis Separations

High-throughput separations were performed in free solution in an Applied Biosystems Prism 3100 capillary array sequencing instrument, with an array of 16 capillaries (effective length 36 cm, total length 47 cm, inner diameter 50 μm). The separations were conducted in 1×TTE buffer (89 mM Tris, 89 mM TAPS, 2 mM EDTA) with 7M urea and 1:100 (v/v) aqueous dilution of the POP-6 polymer solution (ABI) as a wall-coating to suppress electro-osmotic flow and prevent analyte adsorption. Samples were injected electro-kinetically by applying a potential of 1-2 kV (22-44 V/cm) for 5-20 seconds. Electrophoresis was performed at 55° C., with a potential of 15 kV (320 V/cm).

Example 5

—Microfluidic Chip Separations

Free-solution electrophoresis was performed in microfluidic chips, using a custom-built instrument.[38] Microfluidic separations were carried out in straight-channel, borosilicate glass microfluidic chips fabricated by Micronit (Enschede, The Netherlands). The microchannels were 50 µm wide and 20 µm deep with a standard 4-arm, "offset T" design.[39] Internal channel surfaces were coated (to eliminate electroosmotic flow) with an adsorbed layer of poly-N-hydroxyethylacrylamide by pretreating the channels with 1M HCl for 10 minutes, and then flushing with a dilute solution of the polymer for 10 minutes.[40,41] The glass found in these microchips (borofloat) has a significantly different chemical composition than that of fused-silica capillaries. As a result of this chemical difference, the POP-6 polymer solution does not sufficiently coat the surface (from hydrophobic association) to decrease EOF and reduce non-specific binding. Poly-N-hydroxyethylacrylamide, on the other hand, binds to the surface by hydrogen bonding between the polymer and the glass-surface silanol groups.[40,41]

Residual template DNA from the SBE reaction was removed by centrifugal ultrafiltration with a Microcon ultrafiltration device (Millipore, Bedford, Mass.) to achieve successful sample injection on the chip. Injection was accomplished by applying a potential between the sample and waste reservoir in the cross arm to fill the injection zone. After 30 seconds, the potentials were switched to separation mode, causing the material in the injection zone to migrate into the separation channel at a field strength of 530 V/cm. Pullback voltages were applied to prevent sample leakage into the separation channel. A custom-built temperature controller was used to maintain a temperature of 55° C. during the separation.

Results

Genotyping

Figure 2:
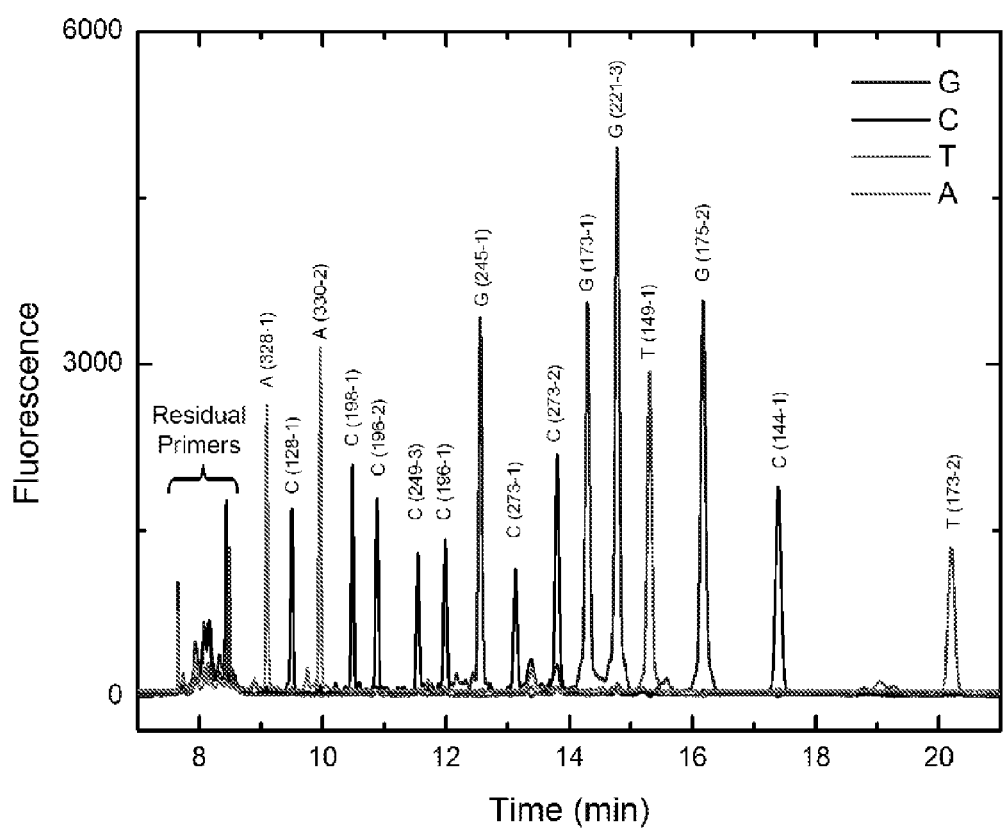
FIG. 2 is a four-color electropherogram showing the FSCE separation of the products of a 16-plex SBE genotyping reaction with a wild-type p53 template. Separations were performed in free aqueous solution on an ABI 3100 CE instrument using a capillary array with an effective length of 36 cm. The buffer was 89 mM Tris, 89 mM TAPS, 2 mM EDTA with 7 M urea. The run temperature was 55° C. Samples were injected electrokinetically at 44 V/cm for 20 seconds. The field strength for the separation was 312 V/cm, with a current of 11 µA per capillary. Each peak is labeled with the corresponding p53 locus and genotype.

The SBE-FSCE compositions and methods as described herein allows for, for example, the simultaneous genotyping of 16 mutation "hot-spots" in p53 exons 5-9 using the 16 different primers described in Table 1, which range in size from 17 to 23 bases. Each primer was conjugated to a monodisperse polyamide drag-tag of unique size, chosen from a set of drag-tags that included 14 different lengths of linear poly (N-methoxyethylglycine) (poly(NMEG)), one branched poly (NMEG) and one genetically engineered protein polymer. A multiplexed SBE reaction with fluorescent ddNTPs extends the primer-drag-tag conjugates by one base, and rapid, high-resolution separation of the bioconjugates by free-solution microchannel electrophoresis allows unambiguous determination of the genotypes simply by the observation of the color of each product peak. As seen in FIG. 2, an exemplary separation of the wild-type p53 SBE products achieved using a commercial CE sequencing instrument is shown. The CE separation gives 16 sharp, well-resolved peaks of different colors, each of which corresponds to the wild-type genotypes shown in Table 1. The identity of each peak and the yield of the conjugation reaction by separate CE analysis of individual drag-tag-primer conjugates were confirmed.

In samples with a point mutation at one or more loci, the corresponding peak(s) change color from those observed for the wild-type sample. For example, in FIG. 3A, the sixth peak is green rather than black, indicating a C to A substitution mutation at locus 249-3. Other templates displayed mixed genotypes at certain loci, as in FIG. 3B, which illustrates peaks of 2 colors at 2 loci. This sample heterozygosity was confirmed by direct sequencing. Notably, these dual genotypes were typically a mixture of wild-type and the expected mutation, indicating that the original sample cell lines contain mixed populations of wild-type and mutant cells.

Figure 3:
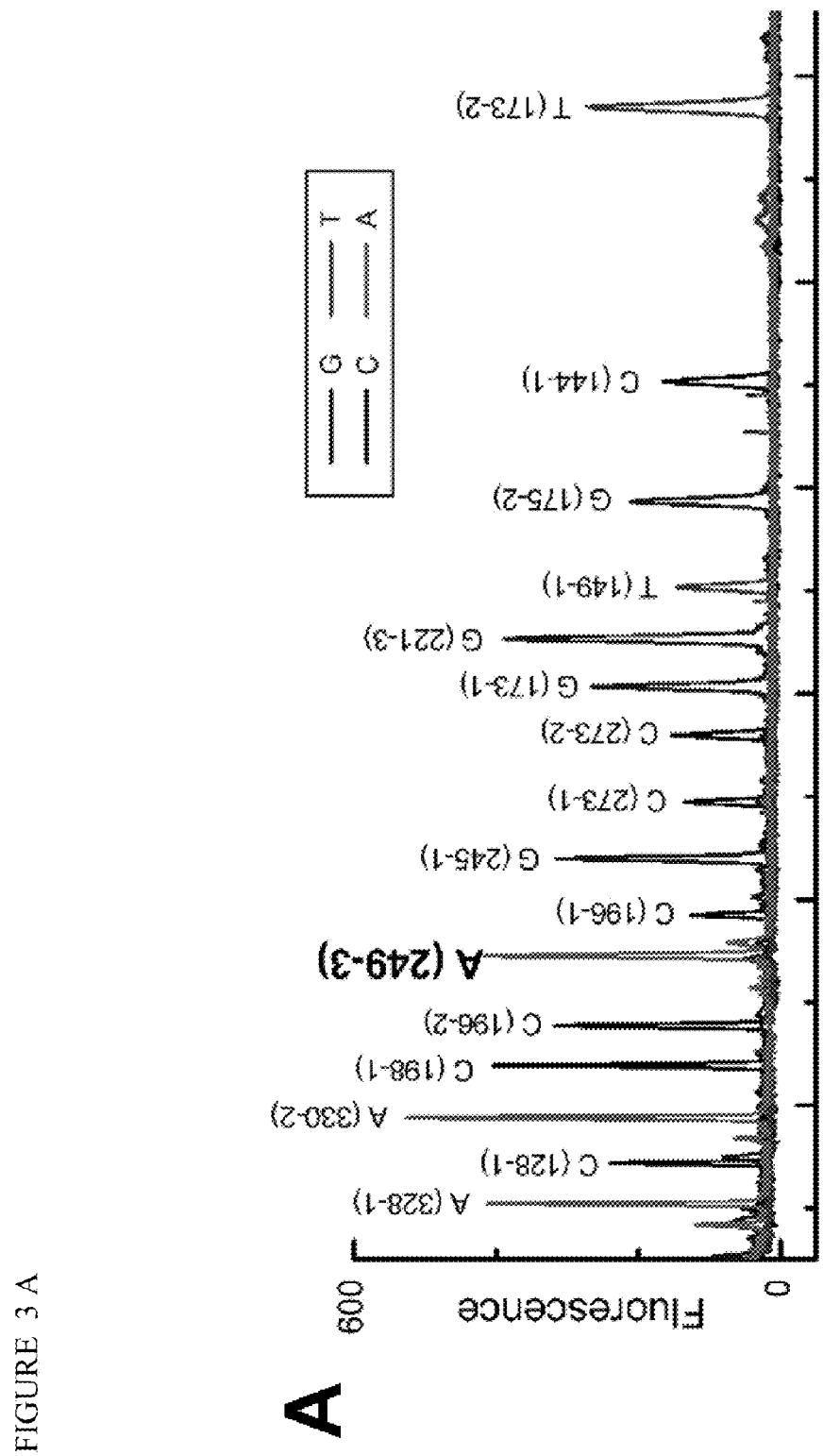
FIG. 3 shows (A) four-color FSCE electropherograms showing the analysis of 16-plex SBE reactions using PCR amplicons of two different p53 variants as templates, with the mutated loci highlighted, including two heterozygotes confirmed by re-sequencing of the mutant template in (B) and pseudo-gel representation of 22 separate SBE-FSCE analyses of p53 variants (C). The wild-type sample is the left-most column, with 21 different mutant samples shown.
Figure 3:
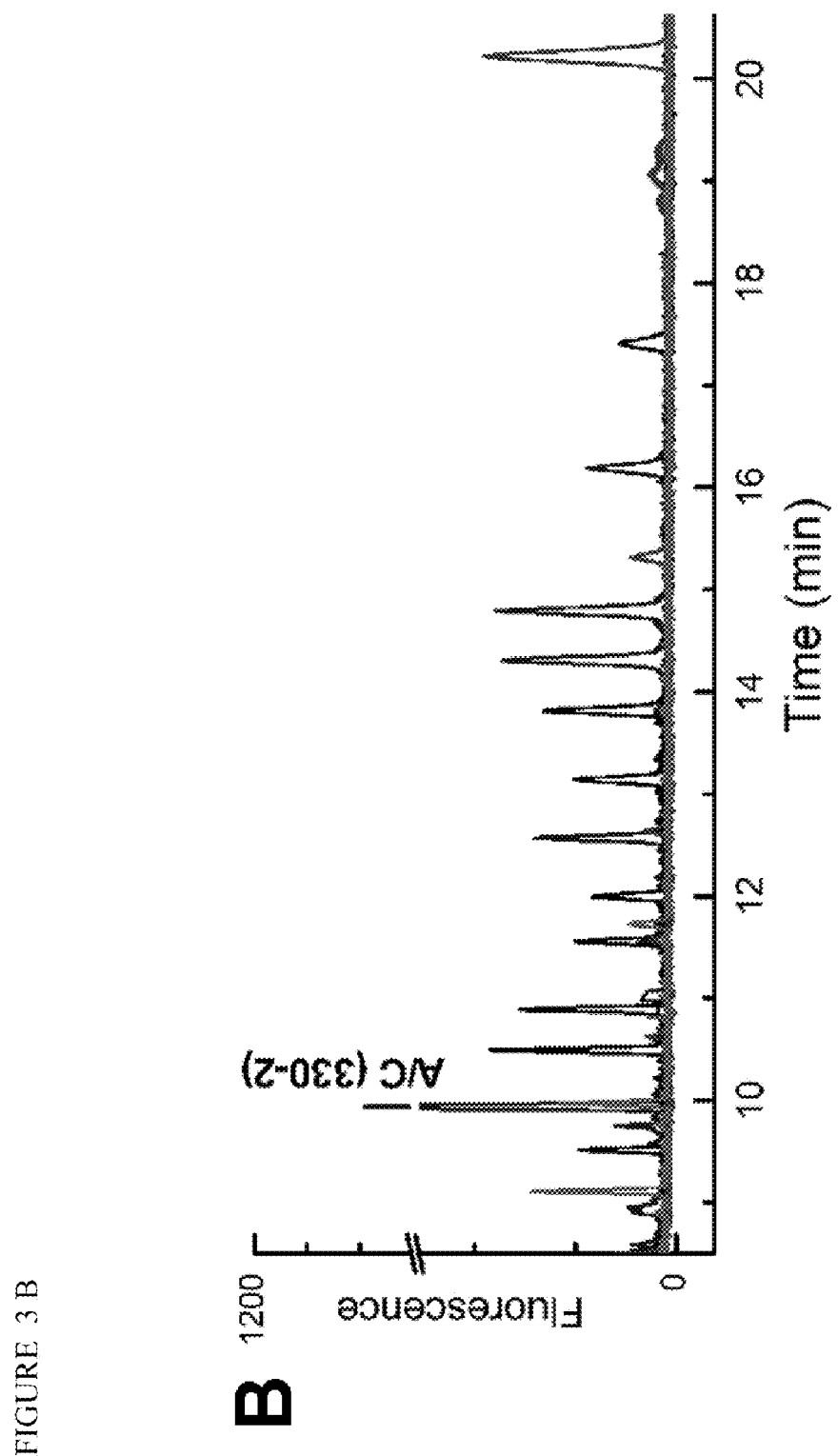
Figure 3:
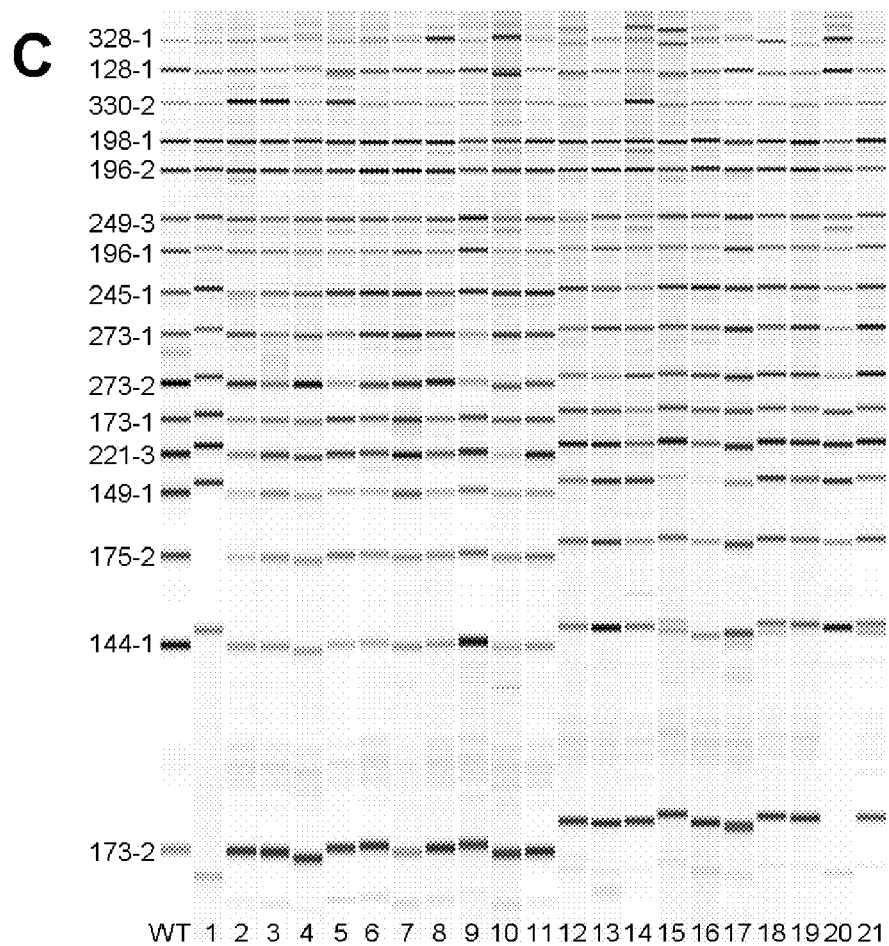

As an exemplary experiment to demonstrate the utility of the compositions and methods as described herein, twenty-two different p53 templates were tested with the resulting electropherograms presented in a "pseudo-gel" format in FIG. 3C, with blue, black, red, and green bands of varying intensity corresponding to the peak heights in the original electropherograms. This representation allows for the rapid comparison and identification of mutations in the different templates, although the original electropherograms (as in FIG. 2, FIG. 3A and 3B) are also useful for identifying possible heterozygotes or low-level peaks that do not show up strongly in the pseudo-gel image.

Of 16 loci across 22 mutant templates (352 loci total), SBE-FSCE correctly and reproducibly genotyped 325 loci. Twenty-seven loci reproducibly gave genotypes that were different from those that were expected based on direct sequencing that had been done at NIST, including 10 apparent heterozygotes. When the original NIST genetic samples were then re-sequenced, 14 of the 27 unexpected genotypes were confirmed to be accurate, including 5 of the 10 apparent heterozygotes; hence, SBE-FSCE more accurately identified these heterozygotes than the original direct sequencing done at NIST. Overall, 339 of the 352 loci were confirmed to be correctly genotyped, representing an accuracy of 96.3% for SBE-FSCE. Accuracies in excess of 99% have been reported for other SBE-based assays,[42] and the molecular biology of the SBE reaction is seemingly not affected by the drag-tag's presence.

Possible interaction or complementarity of the different primers used in a highly multiplexed SBE assay becomes more likely as the level of multiplexing increases; however, sophisticated software for multiplexed primer design is currently used to analyze all possible combinations of primer-dimers for potential stable or extendable structures.[43,44] The issue of primer complementarity presents a difficulty for multiplexing any genotyping assay based on primer extension, and is not specific to the FSCE separation technique as described herein, nor to CE separation and detection in general.

In the preceding examples, primers were dictated by the loci of known mutations in the panel of available cell line samples. Urea (7M) and elevated temperature during the electrophoretic analysis to ensure denaturation of any primer-dimers was performed. It is contemplated that some low-level peaks that did not correspond specifically to any of the individual drag-tagged primers (low-intensity bands in FIG. 3C) were still present, but easily distinguishable from the reaction products. The expected SBE genotyping peaks were the dominant products observed, indicating that the primers annealed preferentially with the template, rather than with each other.

The final primer listed in Table 1 for locus 173-2 included the "universal" base inosine (I) at the 3' end to probe for mutations adjacent to a polymorphic site (locus 173-1), because chain extension following a 3'-mismatch is inefficient. This inosine-containing primer gave the expected genotype (T) for locus 173-2, as can be observed by the topmost red band present for most of the samples depicted in FIG. 3C. However, this strategy was found to be ineffective in the two templates tested with known mutations at locus 173-1 (mutants 1 and 20 in FIG. 3C), with a low efficiency of chain extension and apparently incorrect genotyping results in both cases.

The SBE reaction conditions were modified from the manufacturer's recommended protocol to give optimal performance with the drag-tag labeled primers. The 51.5° C. annealing temperature was determined empirically as the annealing temperature that gave the most even peak heights across all of the loci in the wild-type sample. Only 5 cycles were used in an attempt to shorten the thermal cycling reaction; however reactions with as few as 2 cycles gave sufficient signal in our ABI 3100 CE instrument. The shortened reaction time, along with the addition of a small amount of HCl to the SBE reaction mixture, also alleviated a side reaction which is contemplated to be the base-catalyzed ring-opening of the maleimidopropionic acid linker on the polypeptoid drag-tags.[45] Drag-tags prepared using a Sulfo-SMCC linker (including the branched polypeptoid and the linear protein polymer reported here) are less prone to this side reaction. If signal strength were a limiting factor, a more conventional SBE reaction with 20-25 cycles could be performed using a set of drag-tags prepared with the more stable Sulfo-SMCC linker.

Microfluidic Chip Separations

Figure 4:
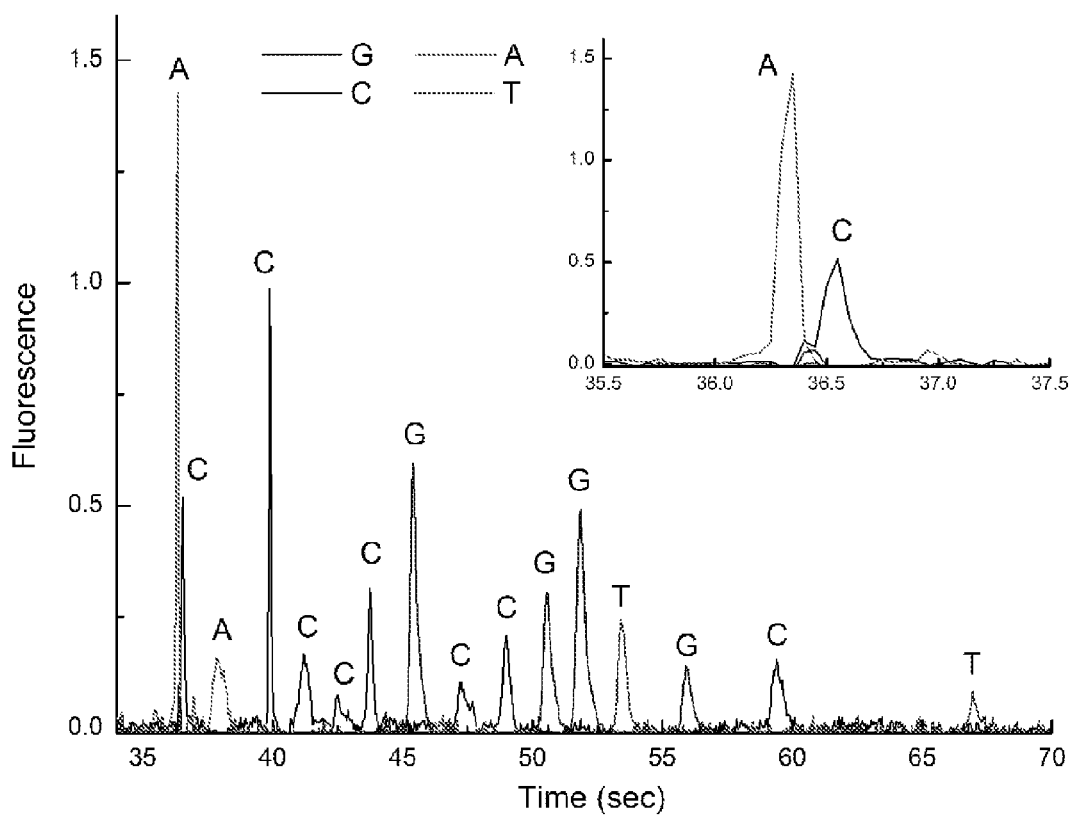
FIG. 4 depicts the separation of a 16plex wild-type p53 SBE sample by free-solution electrophoresis in a glass microfluidic chip, with an adsorbed layer of poly-N-hydroxyethylacrylamide used to coat the interior microchannel's surface to suppress electroosmotic flow and analyte adsorption. The region between 35 and 38 seconds is magnified in the inset to show the distinct elution times of the first "A" and "C" peaks.

FIG. 4 illustrates the exemplary rapid separation of SBE reaction products in a microfluidic electrophoresis chip using the wild-type p53 template. The 16plex SBE-FSCE samples are separated with high resolution in less than 70 seconds in a glass microfluidic device with an effective separation length of 8 cm, approximately 20 times faster than CE. Separations on microfluidic chips are achieved much faster because of the geometry and design of the injection scheme. By using isotachophoretic injection on a chip with a double-T injection geometry,[39] the sample "stacks" into a very narrow, well-defined zone that is readily separated in the 8 cm separation channel of the microfluidic chip. The peak spacing is comparable to that observed with CE, except for the first two peaks that are more closely spaced. As desired, software may be employed to optimize data collection and analysis for a particular system that is employed.

Flexibility of the SBE-FSCE Method

Figure 5:
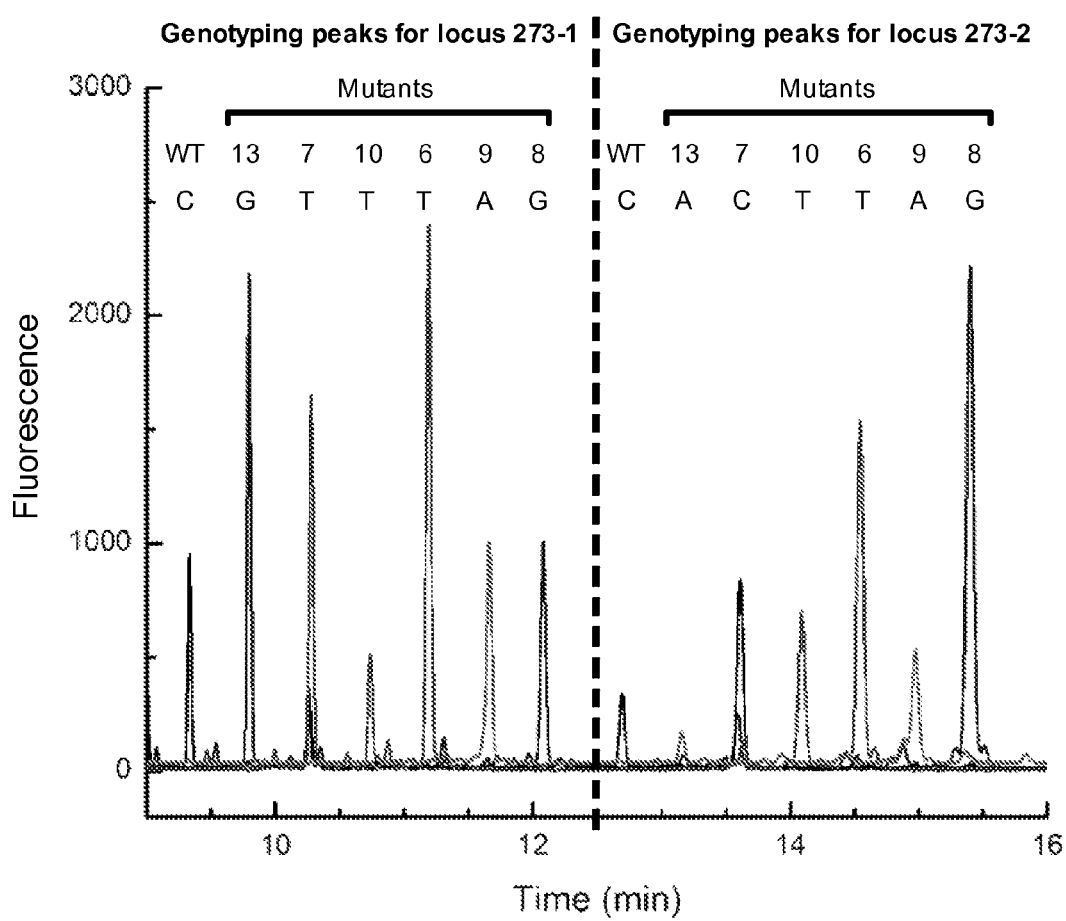
FIG. 5 shows a parallel mutation detection of two p53 loci across seven templates (wild-type and six mutants), with a single electrophoretic analysis separating the pooled reaction products. The mutant sample numbers correspond with those in the pseudo-gel image shown in FIG. 3C.

The polyamide drag-tags and oligonucleotide primers as shown for the examples and described herein are interchangeable; any drag-tag can be paired with any primer to allow tailored conjugates for custom applications. Whereas the specific primer-drag-tag conjugates described in Table 1 allow for multiplexed mutation detection of 16 different loci from the same individual, other tests are possible. For example, many of the mutant samples have mutations at p53 loci 273-1 and 273-2. The genotypes of these 2 loci could be tracked across several different samples in parallel by creating a different multiplexed set of primers. To this end, the primer for locus 273-1 was conjugated to seven different poly-N-methoxyethylglycine (polyNMEG) drag-tags ranging in size from 8 to 32 monomers, and the primer for 273-2 was conjugated to larger drag-tags, 36 to 60 monomers in length. Seven separate SBE reactions were run in parallel with 7 different templates, each using a unique pair of the primer-drag-tag conjugates. The resulting SBE reaction products were then pooled and analyzed by CE in a single capillary (FIG. 5). Since a unique pair of primer-drag-tag conjugates was used for each template, each peak in the electropherogram can be assigned to a specific template and locus. The wild-type is seen to have the genotype "CC", whereas mutant 7 has the genotype "TC", and mutant 8 has the genotype "GG". These results correlate with the results determined by sequencing, and also with the 16plex genotyping reaction result for each mutant sample. This combination of drag-tags and primers allows the 273-1 and 273-2 loci from 96 patient samples to be analyzed in 16 minutes with the 16-capillary ABI 3100, or in approximately 1 minute by microfluidic chip electrophoresis. Any combination of primers is easily paired with any combination of drag-tags. By contrast, conventional CE with polymer matrix-based separation of the SBE reaction products requires custom synthesis of primers with different lengths of DNA "tails" for each situation, so that SBE reaction products (which are very similar in size) are separated by electrophoresis in a gel.[34] A thiolated primer of length 17-24 bases is of comparable cost to a standard primer with a long "tail" but can be used for multiple different applications using FSCE. Protein polymer and poly(NMEG) drag-tags are easily synthesized on a lab-bench scale of tens of milligrams for a modest cost; these amounts being sufficient to perform thousands of the reactions described herein. Thus the drag-tags themselves represent only a small added expense in the SBE-FSCE procedure.

It is contemplated that the degree of multiplexing possible with SBE-FSCE depends primarily on the number of unique drag-tags available, however no fundamental barrier prevents the synthesis of additional unique drag-tags to allow the use of additional primers. It is contemplated that the creation of an arbitrarily large number of unique drag-tags, with the potential for further multiplexing of the SBE-FSCE technique, is primarily limited by the ability to design a suitable set of compatible primers. Multiplexed SBE with simultaneous interrogation of 30 SNPs followed by MALDI-TOF mass spectrometry analysis (requiring primers of easily distinguished molecular weight) has been reported,[18] however the molecular biology of SBE itself (e.g., without utilizing the compositions and methods of the present invention) is incompatible with further multiplexing using the FSCE technique.

In one embodiment, the present invention provides a novel SBE-FSCE technique useful to simultaneously multiplex genotype mismatches with rapid electrophoretic analysis in free solution. For example, as described herein 16 loci on p53 exons 5-9, were genotyped followed by rapid electrophoretic analysis allowing separation of each of the genotyping products in free solution with excellent resolution. As such, high-throughput analysis is achievable with parallel, commercially available capillary array sequencing instruments or miniaturized microfluidic chips. In some embodiments, the method described herein is employed for the detection of point mutations, and as a high-throughput approach for SNP detection.

In one embodiment, the SBE-FSCE compositions and methods as described herein represent a "modular" genotyping approach, applicable to any gene, where the same oligonucleotide primer can be tailored to multiple uses by the facile attachment of different drag-tags. The molecular biology of SBE allows for a very high degree of multiplexing, while FSCE requires each genotyping product to be conjugated to a drag-tag of a unique size and hydrodynamic drag. In some embodiments, the primer design for use in multiplex reactions is performed by a computer software program (e.g., Oligo®, PrimerDesign, etc.).

In some embodiments, microfluidic separation of the SBE-FSCE products is performed in at least 50 seconds, at least 1 minute, in at least 2 minutes, in at least 3 minutes, in at least 4 minutes, in at least 7 minutes.

Example 6

—Production of Protein Polymer Drag-Tags for Sequencing Reactions

A synthetic oligonucleotide encoding for three repeats of the amino acid sequence (Gly-Ala-Gly-Thr-Gly-Ser-Ala) (SEQ ID NO:1) was purchased from Oligos Etc (Wilsonville, Oreg.), and multimerized using the controlled cloning process as previously described (J. I. Won, R. J. Meagher, A. E. Barron, *Electrophoresis* 26, 2138 (2005); I. Won, A. E. Barron, *Macromolecules* 35, 8281 (2002); J. I. Won, R. J. Meagher, A. E. Barron, *Biomacromolecules* 5, 618 (2004)). A multimer encoding 18 repeats of the amino acid sequence was cloned into a modified pET-19B plasmid, isolated and expressed as a fusion protein with an N-terminal polyhistidine tag in *E. Coli*. The fusion protein was recovered from the bacterial cell lysate by immobilized metal affinity chromatography (IMAC) using a nickel chelating resin (Probond, Invitrogen, Carlsbad, Calif.). The N-terminal polyhistidine tag was chemically cleaved using cyanogen bromide in 70% formic acid, and the cleaved protein was purified from residual uncleaved fusion protein and His-tag with a second IMAC step. The target protein was obtained, with the molecular weight confirmed by MALDI-TOF mass spectrometry. DNA sequencing of the gene indicated that two serine to arginine mutations had occurred, thus the actual protein polymer sequence used was (GAGTGSA)$_4$-GAGTGRA-(GAGTGSA)$_7$-GAGTGRA-(GAGTGSA)$_5$G SEQ ID NO:22).

Example 7

—Conjugation of Drag-Tag to DNA Sequencing Primer

The protein polymer was activated at the N-terminus with Sulfo-SMCC by adding a 10:1 molar excess of Sulfo-SMCC to 1.2 mg of the protein in 80 μL of 100 mM sodium phosphate buffer, pH 7.2. The mixture was vortexed for 1 hour, and excess Sulfo-SMCC was removed using a Centri-Sep gel filtration column (Princeton Separations, Adelphia, N.J.). The purified, activated drag-tag was frozen and lyophilized, then resuspended in pure water at a concentration of 10 mg/mL.

A 17 base, thiolated M13(−40) forward sequencing primer (5'-X$_1$GTTTTCCCAGTCACGAC (SEQ ID NO:19), where X$_1$ is a 5'-C6 thiol linker) was purchased from Integrated DNA Technologies (Coralville, Iowa). The 5'-thiol group was reduced by incubating 2 nmol of the DNA with a 20:1 molar excess of TCEP at 40° C. in a total volume of 20 μL of 70 mM sodium phosphate buffer, pH 7.2, for two hours. The reduced oligonucleotide was desalted with a Centri-Sep column, and immediately mixed with a 100-fold molar excess of activated drag-tag in 25 mM sodium phosphate buffer, pH 7.2, with a final DNA concentration of 4.2 pmol/μL. The conjugation reaction was allowed to proceed at room temperature for 4 hours before use. The conjugation yield was estimated at approximately 84% as determined by performing a single-base extension reaction with the conjugated primer, separating the products by free-solution electrophoresis, and measuring the areas of the peaks for conjugated and unconjugated DNA.

Example 8

—Sequencing Reactions and Cleanup

DNA sequencing reactions were carried out using the SNaPshot Multiplex single-base extension (SBE) kit (Applied Biosystems, Foster City, Calif.), with deoxyribonucleotide triphosphates (dNTPs) added to facilitate Sanger sequencing instead of single-base extension. Five μL of the SNaPshot premix was mixed with 8 nmol dNTPs (1.8 nmol dCTP, 1.8 nmol dTTP, 2.2 nmol dGTP, and 2.2 nmol dATP), 4.2 pmol of drag-tag-labeled primer, and 0.16 μg of M13mp 18 control DNA template (Amersham Biosciences, Piscataway, N.J.) in a total volume of 10 μL. The reaction was cycled in a MJ Research Products Thermal Cycler, with 26 cycles of denaturation at 96° C. for 5 seconds, annealing at 50° C. for 5 seconds, and chain extension at 60° C. for 30 seconds. Upon completion of thermal cycling, the reaction products were purified using a Centri-Sep column (Princeton Separations, Adelphia, N.J.) to remove residual buffer salts, dNTPs, and chain terminators. The purified product was diluted to a final volume of 20 μL, and stored at −20° C. until use.

Example 9

—Capillary Electrophoresis

DNA sequencing separations with 4-color LIF detection were performed using an Applied Biosystems Prism 3100 Genetic Analyzer with arrays of 16 fused silica capillaries with inner diameters of 50 cm and effective lengths (from inlet to the detector) of 36, 50, or 80 cm (total lengths of 47, 61, or 91 cm). Separations were carried out at 55° C. in a denaturing buffer consisting of 1×TTE (89 mM Tris, 89 mM TAPS, 2 mM EDTA) with 7 M urea, and 0.5% v/v POP-5 solution (PDMA) added as a dynamic wall coating agent. The buffer was filtered with a 0.45 μm filter prior to use. The capillary was flushed with fresh buffer between each run, and the buffer reservoirs were replenished every 1-3 runs.

Sequencing samples were denatured prior to analysis by heating (in water) to 95° C. for 30 seconds, followed by snap cooling on ice. Samples were introduced into the capillaries by electrokinetic injection at 1 kV for 20 seconds. Run voltages ranging from 3 to 15 kV were tested, with emission from the SNaPshot dRhodamine terminators detected using ABI Dye Set E5.

Results

In the standard theory of FSCE (C. Desruisseaux, D. Long, G. Drouin, G. W. Slater, *Macromolecules* 34, 44 (2001); L. C. McCormick et al., *Journal of Chromatography A* 924, 43 (2001); R. J. Meagher et al., *Electrophoresis* 26, 331 (2005)), the electrophoretic mobility of a composite object is determined by a weighted average of the electrophoretic mobilities of charged DNA and uncharged drag-tag monomers. Mathematically, this weighted average mobility for a chain with $M_c$ charged DNA monomers and $M_u$ uncharged monomers is:

$$\mu = \mu_0 \frac{M_c}{M_c + \alpha_1 M_u} \quad (1)$$

Wherein $\mu_0$ is the free-solution electrophoretic mobility of DNA (independent of size), and $\alpha_1$ is a weighting factor that rescales the number of uncharged monomers based on differences in size and persistence length as compared to the DNA monomers.

Uncharged polymer chains are considerably more flexible than ssDNA, and typical values of $\alpha_1$ range from 1/5 to 1/6. The product $\alpha \equiv \alpha_1 M_u$ has frequently been used to characterize the overall drag provided by a drag-tag, and can be calculated from experimental data.

A controlled cloning technique (J. I. Won, A. E. Barron, *Macromolecules* 35, 8281 (2002)) was utilized to create an artificial gene encoding for a repetitive protein polymer with the repeating sequence (GAGTGSA)$_{18}$G (SEQ ID NO:21), with the final sequence being (GAGTGSA)$_4$-GAGTGRA-(GAGTGSA)$_7$-GAGTGRA-(GAGTGSA)$_5$-G SEQ ID NO:22). DNA sequencing confirmed the sequence of the gene. This biochemical change to the designed amino acid sequence, with the addition of two arginine residues, increased the net charge of the protein polymer by +2 units, which did not strongly affect the final properties of the drag-tag. Following Sulfo-SMCC activation of the amino terminus, the original protein polymer sequence would have yielded a net charge of −1 (from the carboxyl terminus), whereas the two arginine mutations give the drag-tag a net charge of +1.

Although positively charged drag-tags have been contemplated to exhibit problems with ionic interaction between the drag-tag and capillary walls or DNA, the very slight positive charge of this drag-tag did not lead to such problems. The drag-tag experiences an electrical force in the opposite direction of the DNA, resulting in a slight "tug" opposing the motion of the DNA, and the net effect is contemplated to be dramatic (one positively charged residue provides a similar effect to 5-6 uncharged amino acids). Thus, drag-tags with a slight positive charge are recommended with caution as it is contemplated that a critical amount of positive charge exists above which the ionic interactions between the drag-tag and capillary, or drag-tag and DNA, decrease the separation performance.

The ABI SNaPshot kit, intended for single-base extension genotyping reactions, was converted to a DNA sequencing kit by the addition of dNTPs. Addition of different amounts of dNTPs allows generation of sequencing reads of varying lengths, with a certain amount of empirical investigation required to determine the appropriate level for a desired read length. A total concentration of 800 μM dNTPs in the sequencing reaction generated a ladder of sequencing products up to about 250 bases long, an appropriate size range for this small drag-tag. A slightly skewed distribution of the four dNTPs (220 μM dGTP and dATP, 180 μM dCTP and dTTP) led to slightly more even peak heights than was obtained using equal concentrations of each dNTP. A sequencing reaction with a common sequencing "premix" kit (BigDye v3.1, ABI) was also performed, however the large size distribution of the sequencing products was not optimal for the drag-tag.

The examples show that the sequencing reaction can be performed with the protein polymer drag-tag attached to the sequencing primer, and that the presence of the drag-tag does not interfere with the action of the sequencing polymerase, or disrupt the stability of the primer-template-enzyme complex. As seen previously with streptavidin (H. Ren et al., *Electrophoresis* 20, 2501 (1999)), thermal cycling was performed in the absence of streptavidin, and the resulting sequencing products were conjugated to streptavidin afterward because the high temperature of the sequencing reaction would lead to irreversible denaturation and aggregation of streptavidin. Whereas conjugation to streptavidin after the sequencing reaction is dependent upon exactly the right ratio of streptavidin to DNA, conjugation beforehand allows precise characterization of the extent of conjugation prior to the sequencing reaction.

A typical sequencing electropherogram, obtained in a capillary with an effective length of 36 cm, at a field strength of 312 V/cm, was demonstrated. The smaller fragments are resolved far more than necessary for unambiguous identification of each base. Determination of the sequence is straight-forward, up to $M_c \approx 115$, although slight mobility shifts introduced by the different dye terminators cause certain peaks to overlap, or even elute in the reverse order. Specifically, the G-terminated fragments elute slightly earlier than expected, causing some ambiguities. The G-terminated fragments have slightly lower resolution than fragments terminated with other bases. Beyond about 120 bases, the mobility shifts and unresolved peaks for repeated bases make identification of the sequence less easy, however since the M13mp18 sequence is known a priori, the observed peaks can be aligned with the known sequence to at least 180 bases with minimal effort. As has been done with existing commercial automated sequencing systems, software can also be used to adjust for discrepancies in certain ranges of the reaction to enhance accurate base calls. For a truly unknown template, it is contemplated that more data processing techniques may be used to correct for the mobility shifts of the different terminators (as is commonly done for gel-based sequencing) and analyze peak widths to determine if a single broad peak might represent two or more repeated bases.

When compared to previous streptavidin sequencing results (H. Ren et al., *Electrophoresis* 20, 2501 (1999)), the compositions and methods of the present invention demonstrate sharper, cleaner peaks and significantly better resolution with the protein polymer drag-tag. This is observed by comparing distinctive features such as the CCCCGGG run at 75-81 bases, or the TAAT peaks at 99-102 bases, both of which display sharper, better-resolved peaks than the streptavidin sequencing results.

Figure 6:
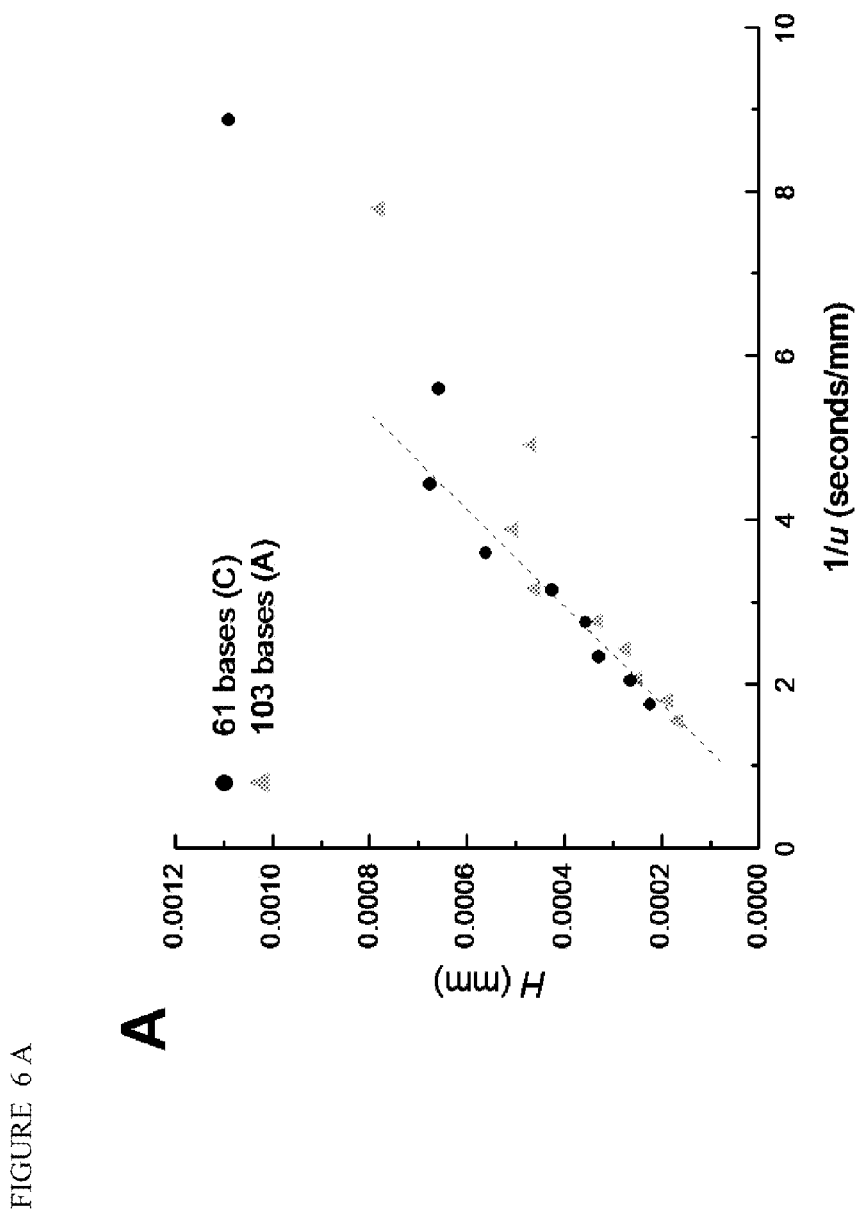
FIG. 6 shows the effect of various parameters on the quality of electrophoretic separation. (A) Theoretical plate height H as a function of the inverse of electrophoretic velocity u for the 61- and 103-base sequencing fragments. Electric field strength was varied between 60 and 310 V/cm; (B) Plate height H as a function of capillary length. The electric field was varied to give similar velocities in each length of capillary. Values of H for the 36- and 50-cm capillaries were interpolated from nearby values to match the velocities observed in the 80-cm capillary. (C) Resolution R, as defined by Equation (5), calculated for selected pairs of closely eluting DNA fragments terminated with the same base. Separations were performed in capillaries with effective lengths of 36, 50, and 80 cm (total lengths of 47, 61, and 91 cm) at an applied potential of 14.7 kV, with all other conditions as described in FIG. 6. The dotted line at R=1 indicates the threshold value below which peaks can be considered well-resolved. (D) Effect of buffer concentration on the drag parameter $\alpha_1$. The solid curve is drawn to guide the eye. Buffer concentration 1×≡(89 mM Tris, 89 mM TAPS, 2 mM EDTA); all buffers include 7M urea and 0.5% v/v POP-5 solution. Separation conditions are as described in FIG. 6, except the separation voltage was 11.3 kV (240 V/cm).
Figure 6:
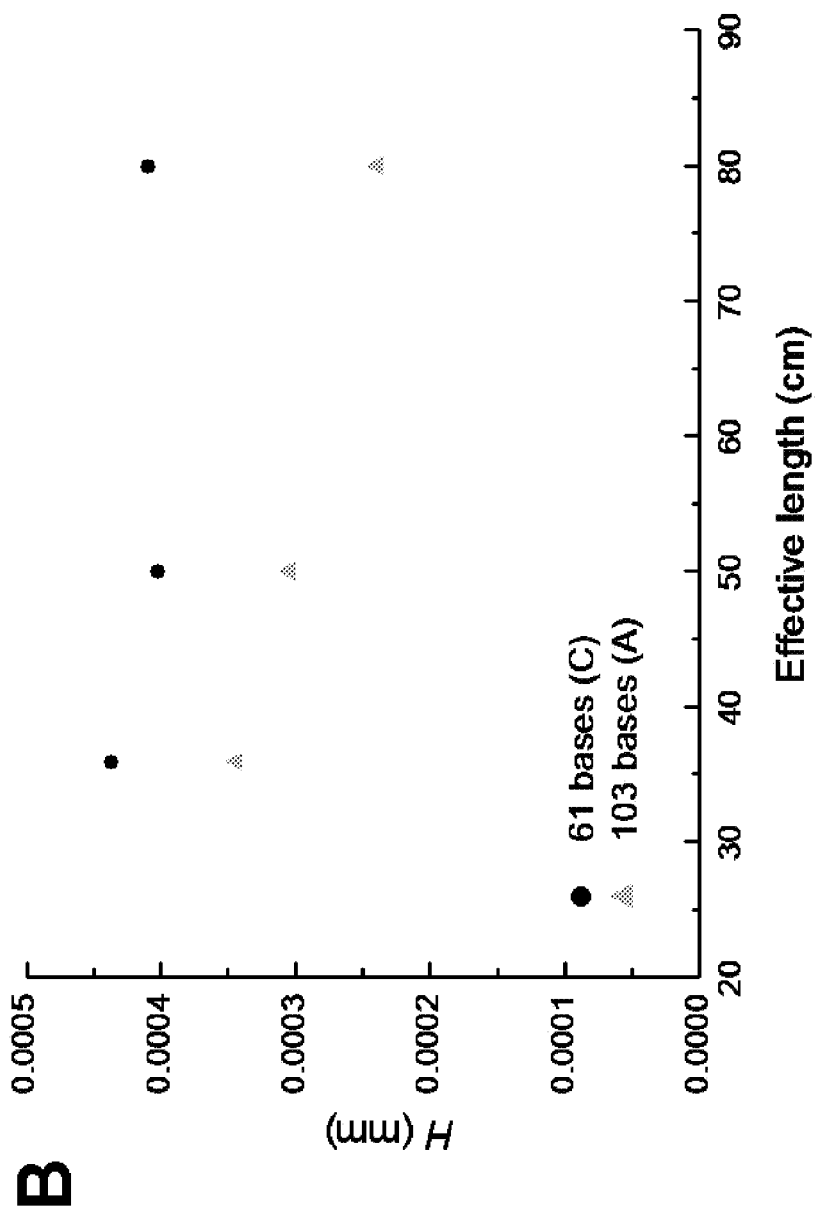
Figure 6:
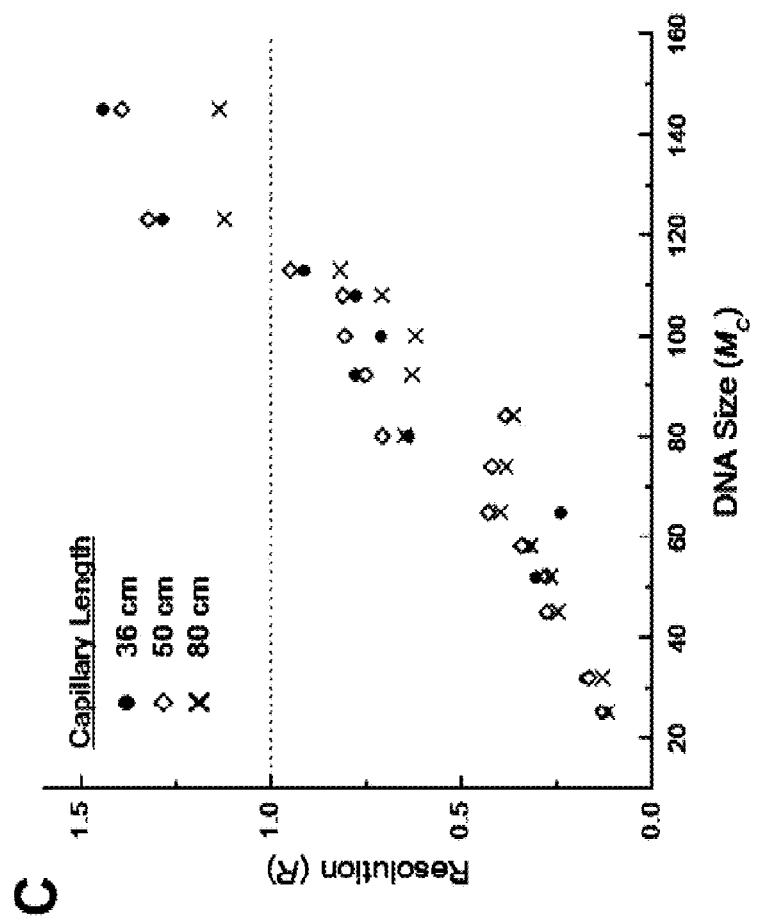
Figure 6:
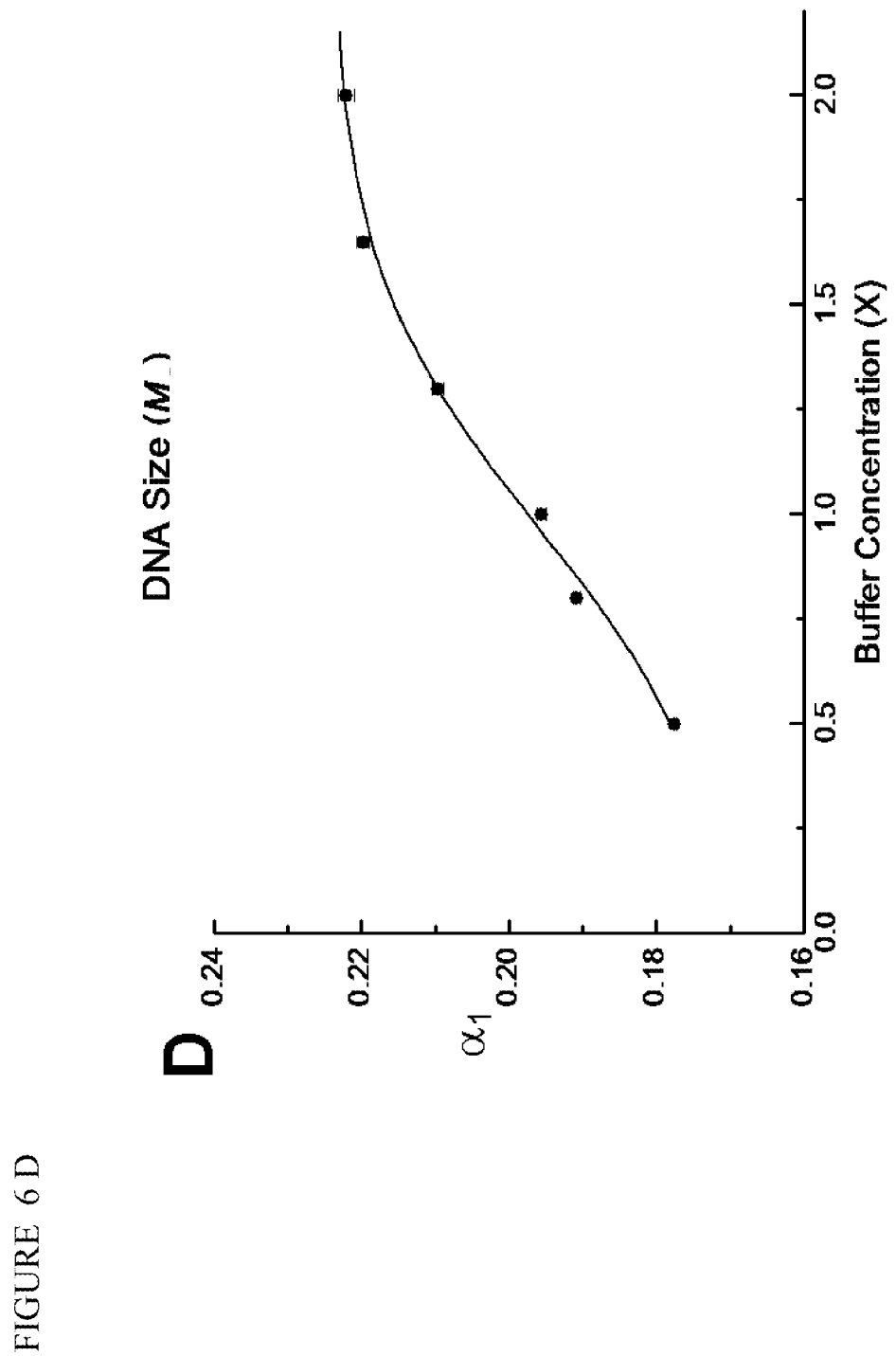

Following the standard theory of FSCE as described herein, a rearrangement of Equation (1) indicates that a plot of $(\mu_0/\mu-1)$ versus $1/M_c$ gives a straight line with a slope equivalent to $\alpha = \alpha_1 M_u$. Sequencing data (plotted) in FIG. 6 is linear, with an overall slope of 25.0±0.05. Slight curvature is apparent at either end of the data set, and is contemplated to result from the influence of end effects that were ignored in the derivation of Equation (1) (D. Long, A. V. Dobrynin, M. Rubinstein, A. Ajdari, *Journal of Chemical Physics* 108, 1234 (Jan. 15, 1998); L. C. McCormick, G. W. Slater, *Electrophoresis* 26, 1659 (2005)). Linear fitting of the fragments labeled with each terminator separately yields slightly different α values for each dye terminator, which are contemplated to result from differences in hydrodynamic properties or net charge for each of the dye terminators. These slight differences in α correlate with the mobility shifts for the different terminators observed.

Several factors lead to an observation of band broadening in FSCE, including the initial injection zone width, analyte-wall interactions, polydispersity of the drag-tag, and thermal diffusion. Following the approach of H. Ren et al., *Electrophoresis* 20, 2501 (1999), the relative magnitudes of the different effects upon the theoretical plate height H are quantified using an equation akin to the van Deemter equation of chromatography:

$$H = \frac{A}{L} + \frac{2D}{u} + Wu + BL \quad (2)$$

wherein L and u refer to the effective length of the capillary and the electrophoretic velocity,
D is the diffusion coefficient, and
A, W, and B are constants related to the magnitudes of injection plug width, analyte-wall interactions, and polydispersity of the drag-tag, respectively.

The height of a theoretical plate is related to peak broadness and for Gaussian peaks the plate height H is determined from the peak elution time, peak width, and capillary length. By independently varying either L or u, and calculating H for a given size of DNA, the relative contributions of the different effects on band broadening can thus be determined using Equation (2). Ideally, for a narrow injection zone and a monodisperse, non-adsorbing drag-tag, the primary contribution to band-broadening is diffusion.

In addition to the plate height H, the resolution between adjacent peaks is considered for determining read lengths. The resolution factor R is the ratio of peak width at half-maximum to the spacing between two peaks. The resolution for two peaks for DNA of size $M_1$ and $M_2$ can be defined as:

$$R = \frac{(w_1 + w_2)}{2} \frac{(M_2 - M_1)}{(t_1 - t_2)} \quad (3)$$

wherein $w_1$ and $w_2$ refer to the peak widths, and
$t_1$ and $t_2$ refer to the peak elution times.
In practice, peaks for which $R \leq 1$ are well-resolved, whereas peaks for which $R > 1$ are run together, makes determining sequence difficult.

Using a capillary array with an effective length of 36 cm (total length of 47 cm), the electrophoretic velocity was varied by adjusting the applied voltage between 3 kV and 15 kV, the maximum allowed by the instrument. The electrophoretic velocity u and theoretical plate height H were tracked for two sizes of DNA, $M_c=61$ and 103 (terminated by C and A, respectively). The two sizes were chosen in part because the same two sizes were tracked by Ren et al. in their experiments, allowing a direct comparison between the two studies, and also because these peaks are relatively isolated from other C- or A-terminated fragments, allowing easy identification and estimation of peak width. The electrophoretic velocities u for these two fragments increased linearly with the electric field strength. No curvature was apparent in the behavior of velocity with field strength, indicating that the drag-tag-DNA conjugate behaves as a random coil object (without segregation of the drag-tag from the DNA) over the entire range of field strengths.

Theoretical plate heights H for the two sizes of DNA-drag-tag conjugates are plotted with respect to the inverse of velocity (1/u) in FIG. 6A. The plate heights H for both sizes of DNA are linear with respect to 1/u for all but the lowest velocities tested, with an intercept approaching zero at high velocity (i.e. as 1/u approaches zero). According to Equation (2), this indicates that diffusion is the primary contributor to band-broadening at these conditions. The measured slope of $1.7 \times 10^{-4}$ mm$^2$/s suggests a diffusion coefficient D of about $8.5 \times 10^{-7}$ cm$^2$/s for the DNA-drag-tag conjugates, which correlates well with diffusion coefficients for DNA fragments of similar size measured during free-solution electrophoresis by Nkodo et al (A. E. Nkodo et al., *Electrophoresis* 22, 2424 (2001)).

Sequencing separations were performed with three different lengths of capillary arrays, with 36, 50, and 80 cm effective lengths. Unlike the ABI 310 instrument used by Ren et al (H. Ren et al., *Electrophoresis* 20, 2501 (1999)), for which many different lengths of capillary may be used, the ABI 3100 offers only four choices: the three as used herein, along with a short, 22 cm array, at a considerable expense for each array. As with electrophoretic velocity, plate heights were calculated for the 61- and 103-base, C- and A-terminated DNA fragments and plotted with respect to capillary length (at constant electrophoretic velocity u) in FIG. 6B. Some low-level peaks that arise from the heterogeneity of the drag-tag can be observed in the electropherogram. These do not interfere with identification of small DNA fragments, but the extra peaks become compressed for larger fragments resulting in an uneven, elevated baseline that can make identification of the peaks difficult.

According to the standard theory of FSCE, the resolution of diffusion-limited FSCE separations is independent of capillary length L, with dependence instead on the total applied potential (the product EL). This is different from many other electrophoretic or chromatographic separations, for which resolution increases with L, typically raised to some fractional power. The resolution R is plotted as a function of DNA size in FIG. 6C for each length of capillary at a total applied potential of 14.7 kV. The read-length is approximated as the point at which R=1, which occurs between $M_c=110$ and 120 bases, although more advanced base calling software is capable of accurately identifying cases where a single broad peak represents two or more identical bases in a row. The values of R are similar for both 36- and 50-cm capillaries, and slightly better for the 80-cm capillary. Although the uncertainty inherent in measurements of R is large, detailed comparisons of the electropherograms for the different lengths of capillary tubes indicate narrower peaks separated by deeper valleys for the 80-cm capillaries, suggesting that the better resolution for the 80-cm case is real.

The friction parameter α, or more fundamentally the product $\alpha_1 M_u$, is a relative quantity that depends on the properties of the charged and uncharged monomers. Specifically, as described in R. J. Meagher et al., *Electrophoresis* 26, 331 (January, 2005) $\alpha_1$ depends on the ratio of sizes of the uncharged and charged monomers and the ratio of Kuhn lengths (related to chain stiffness) of the uncharged and charged monomers. Although the monomer sizes are fixed by their chemical structures, the ratio of Kuhn lengths depends on the solution conditions. It is contemplated that increasing ionic strength decreases the Kuhn length of DNA without significantly affecting the drag-tag, thereby increasing $\alpha_1$ (C. Desruisseaux, D. Long, G. Drouin, G. W. Slater, *Macromolecules* 34, 44 (2001)).

To measure this effect, exemplary sequencing separations were performed with TTE buffer concentrations varying by a factor of 4, from 0.5× to 2×. The resulting electropherograms were used to calculate the values of $\alpha_1$ for each buffer concentration, with results shown in FIG. 6D. As found previously for streptavidin, the value of $\alpha_1$ depends on ionic strength, increasing by 20% over the concentration range studied.

Although increasing the ionic strength has an impact on the friction imposed by the drag-tag, it is not clear that this leads to increased sequencing performance for high ionic strengths, as no consistent trend between the buffer ionic strength and the resolution was seen. It is contemplated that heat generation caused by high current with high ionic strength buffers degrades sequencing performance, despite the larger values of $\alpha_1$. It is contemplated that the optimum buffer concentration involves a tradeoff between increased a (high ionic strength) and decreased current (low ionic strength), with the requirement of good buffering capacity imposing a constraint on the minimum buffer concentration. It is further contemplated that the capillary inner diameter is also subject to optimization, as heat removal is optimal in narrower capillaries, allowing for the use of buffers with higher ionic strength or higher electric fields.

As such, the first major progress in FSCE sequencing since the first report of sequencing with streptavidin in 1999 by Ren et al. (H. Ren et al., *Electrophoresis* 20, 2501 (1999)) is exemplified herein. The protein polymer drag-tag compositions as described have an effective drag similar to streptavidin, with a of about 25, however compositions of the present invention yield significantly cleaner results, with sharper peaks. The compositions of the present invention can therefore be used successfully for DNA sequencing. For example, the presence of a 127-amino acid long protein polymer attached to the short (17 base) sequencing primer does not interfere with the ability of the primer to hybridize to the template, or with the chain elongation activity of the sequencing polymerase.

It is further contemplated that FSCE and the compositions and methods as described herein are amenable to sequencing on microfluidic devices, which offer numerous advantages and greater flexibility than capillary sequencing instruments.

All publications and patents mentioned in the present application are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

REFERENCES (1) Collins, F. S.; Brooks, L. D.; Chakravarti, A. *Genome Research* 1998, 8, 1229-1231.
(2) Brookes, A. J. *Gene* 1999, 234, 177-186.
(3) Strittmatter, W. J.; Saunders, A. M.; Schmechel, D.; Pericakvance, M.; Enghild, J.; Salvesen, G. S.; Roses, A. D. *Proceedings of the National Academy of Sciences of the United States of America* 1993, 90, 1977-1981.
(4) Strittmatter, W. J.; Roses, A. D. *Proceedings of the National Academy of Sciences of the United States of America* 1995, 92, 4725-4727.
(5) Greenblatt, M. S.; Bennett, W. P.; Hollstein, M.; Harris, C. C. *Cancer Research* 1994, 54, 4855-4878.
(6) Soussi, T.; Beroud, C. *Nature Reviews Cancer* 2001, 1, 233-240.
(7) Soussi, T.; Lozano, G. *Biochemical and Biophysical Research Communications* 2005, 331, 834-842.
(8) Birch, J. M.; Alston, R. D.; McNally, R. J.; Evans, D. G.; Kelsey, A. M.; Harris, M.; Eden, O. B.; Varley, J. M. *Oncogene* 2001, 20, 4621-4628.
(9) Olivier, M.; Goldgar, D. E.; Sodha, N.; Ohgaki, H.; Kleihues, P.; Hainaut, P.; Eeles, R. A. *Cancer Research* 2003, 63, 6643-6650.
(10) Kirk, B. W.; Feinsod, M.; Favis, R.; Kliman, R. M.; Barany, F. *Nucleic Acids Research* 2002, 30, 3295-3311.
(11) Landegren, U.; Nilsson, M.; Kwok, P. Y. *Genome Research* 1998, 8, 769-776.
(12) Chen, X.; Sullivan, P. F. *Pharmacogenomics Journal* 2003, 3, 77-96.
(13) Syvanen, A. C.; Aaltosetala, K.; Harju, L.; Kontula, K.; Soderlund, H. *Genomics* 1990, 8, 684-692.
(14) Pastinen, T.; Partanen, J.; Syvanen, A. C. *Clinical Chemistry* 1996, 42, 1391-1397.
(15) Pastinen, T.; Kurg, A.; Metspalu, A.; Peltonen, L.; Syvanen, A. C. *Genome Research* 1997, 7, 606-614.
(16) Sanger, F.; Nicklen, S.; Coulson, A. R. *Proceedings of the National Academy of Sciences of the United States of America* 1977, 74, 5463-5467.
(17) Ross, P.; Hall, L.; Smirnov, I.; Haff, L. *Nature Biotechnology* 1998, 16, 1347-1351.
(18) Kim, S.; Ulz, M. E.; Nguyen, T.; Li, C. M.; Sato, T.; Tycko, B.; Ju, J. *Genomics* 2004, 83, 924-931.
(19) Bell, P. A.; Chaturvedi, S.; Gelfand, C. A.; Huang, C. Y.; Kochersperger, M.; Kopla, R.; Modica, F.; Pohl, M.; Varde, S.; Zhao, R. B.; Zhao, X. J.; Boyce-Jacino, M. T. *Biotechniques* 2002, 32, S70-S77.
(20) Makridakis, N. M.; Reichardt, J. K. V. *Biotechniques* 2001, 31, 1374-1380.
(21) Mayer, P.; Slater, G. W.; Drouin, G. *Analytical Chemistry* 1994, 66, 1777-1780.
(22) Heller, C.; Slater, G. W.; Mayer, P.; Dovichi, N.; Pinto, D.; Viovy, J. L.; Drouin, G. *Journal of Chromatography A* 1998, 806, 113-121.
(23) Ren, H.; Karger, A. E.; Oaks, F.; Menchen, S.; Slater, G. W.; Drouin, G. *Electrophoresis* 1999, 20, 2501-2509.
(24) Meagher, R. J.; Won, J. I.; McCormick, L. C.; Nedelcu, S.; Bertrand, M. M.; Bertram, J. L.; Drouin, G.; Barron, A. E.; Slater, G. W. *Electrophoresis* 2005, 26, 331-350.
(25) Grossman, P. D. F.; Menchen, S. M.; Woo, S. L.; Winn-Deen, E. S.: World, 1993.
(26) Noolandi, J. *Electrophoresis* 1992, 13, 394-395.
(27) Vreeland, W. N.; Desruisseaux, C.; Karger, A. E.; Drouin, G.; Slater, G. W.; Barron, A. E. *Analytical Chemistry* 2001, 73, 1795-1803.
(28) Vreeland, W. N.; Slater, G. W.; Barron, A. E. *Bioconjugate Chemistry* 2002, 13, 663-670.
(29) Won, J. I.; Meagher, R. J.; Barron, A. E. *Electrophoresis* 2005, 26, 2138-2148.
(30) Haynes, R. D.; Meagher, R. J.; Won, J. I.; Bogdan, F. M.; Barron, A. E. *Bioconjugate Chemistry* 2005, 16, 929-938.
(31) Sudor, J.; Novotny, M. V. *Analytical Chemistry* 1997, 69, 3199-3204.
(32) Sudor, J.; Novotny, M. V. *Analytical Chemistry* 1995, 67, 4205-4209.
(33) Vreeland, W. N.; Meagher, R. J.; Barron, A. E. *Analytical Chemistry* 2002, 74, 4328-4333.
(34) Sanchez, J. J.; Phillips, C.; Borsting, C.; Balogh, K.; Bogus, M.; Fondevila, M.; Harrison, C. D.; Musgrave-Brown, E.; Salas, A.; Syndercombe-Court, D.; Schneider, P. M.; Carracedo, A.; Morling, N. *Electrophoresis* 2006, 27, 1713-1724.
(35) Zuckermann, R. N.; Kerr, J. M.; Kent, S. B. H.; Moos, W. H. *Journal of the American Chemical Society* 1992, 114, 10646-10647.
(36) Won, J. I.; Barron, A. E. *Macromolecules* 2002, 35, 8281-8287.
(37) Won, J. I.; Meagher, R. J.; Barron, A. E. *Biomacromolecules* 2004, 5, 618-627.
(38) Chiesl, T. N.; Shi, W.; Barron, A. E. *Analytical Chemistry* 2005, 77, 772-779.
(39) Shultz-Lockyear, L. L.; Colyer, C. L.; Fan, Z. H.; Roy, K. I.; Harrison, D. J. *Electrophoresis* 1999, 20, 529-538.
(40) Albarghouthi, M. N.; Buchholz, B. A.; Huiberts, P. J.; Stein, T. M.; Barron, A. E. *Electrophoresis* 2002, 23, 1429-1440.
(41) Albarghouthi, M. N.; Stein, T. M.; Barron, A. E. *Electrophoresis* 2003, 24, 1166-1175.
(42) Hirschhorn, J. N.; Sklar, P.; Linbland-Toh, K.; Lim, Y.-M.; Ruiz-Guiterrez, M.; Bolk, S.; Langhorst, B.; Schaffner, S.; Winchester, E.; Lander, E. S. *Proceedings of the National Academy of Sciences of the United States of America* 2000, 97, 12164-12169.

(43) Rachlin, J.; Ding, C. M.; Cantor, C.; Kasif, S. *Nucleic Acids Research* 2005, 33, W544-W547.

(44) Kaderali, L.; Deshpande, A.; Nolan, J. P.; White, P. S. *Nucleic Acids Research* 2003, 31, 1796-1802.

(45) Hermanson, G. *Bioconjugate Techniques*; Academic Press, Inc: San Diego, Calif., 1996.

(46) Paegel, B. M.; Blazej, R. G.; Mathies, R. A. *Current Opinion in Biotechnology* 2003, 14, 42-50.

(47) Paegel, B. M.; Yeung, S. H. I.; Mathies, R. A. *Analytical Chemistry* 2002, 74, 5092-5098.

(48) Ferrance, J. P.; Wu, Q. R.; Giordano, B.; Hernandez, C.; Kwok, Y.; Snow, K.; Thibodeau, S.; Landers, J. P. *Analytica Chimica Acta* 2003, 500, 223-236.

---

We claim:

1. A method for the detection of single nucleotide polymorphisms comprising:
   a) providing one or more DNA samples to be tested,
   b) providing eight or more DNA-polyamide bioconjugates specific to one or more single nucleotide polymorphisms, wherein said eight or more DNA-polyamide bioconjugates each comprise a primer sequence linked to one of eight or more different polyamide drag-tags that differ in size, wherein said eight or more different polyamide drag-tags comprise methoxyethylglycine (NMEG) monomers, and wherein each of said eight or more different polyamide drag-tags has a size that differs by no more than 4 NMEG monomers from the size of the other drag-tag(s) closest in size;
   c) contacting said DNA sample with said DNA-polyamide bioconjugates,
   d) performing a single nucleotide polymorphism assay on said DNA sample, wherein said assay is conducted under conditions that generate reaction products that are individually resolvable in a free-solution electrophoresis instrument,
   e) applying said DNA sample to a free-solution electrophoretic instrument under conditions such that said eight or more DNA-polyaminde bioconjugates are separated from each other in said free-solution electrophoretic instrument, and
   f) detecting the presence or absence of a single nucleotide polymorphism in said DNA sample.

2. The method of claim 1, wherein said single nucleotide polymorphism assay comprises a single-base-extension (SBE) assay.

* * * * *

SEQUENCE LISTING

<160> NUMBER OF SEQ ID NOS: 22

<210> SEQ ID NO 1
<211> LENGTH: 7
<212> TYPE: PRT
<213> ORGANISM: Artificial Sequence
<220> FEATURE:
<223> OTHER INFORMATION: Synthetic

<400> SEQUENCE: 1

Gly Ala Gly Thr Gly Ser Ala
1               5

<210> SEQ ID NO 2
<211> LENGTH: 36
<212> TYPE: PRT
<213> ORGANISM: Artificial Sequence
<220> FEATURE:
<223> OTHER INFORMATION: Synthetic

<400> SEQUENCE: 2

Gly Ala Gly Thr Gly Ser Ala Gly Ala Gly Thr Gly Arg Ala Gly Ala
1               5                   10                  15

Gly Thr Gly Ser Ala Gly Ala Gly Thr Gly Arg Ala Gly Ala Gly Thr
            20                  25                  30

Gly Ser Ala Gly
        35

<210> SEQ ID NO 3
<211> LENGTH: 23
<212> TYPE: DNA
<213> ORGANISM: Artificial Sequence
<220> FEATURE:
<223> OTHER INFORMATION: Synthetic

<400> SEQUENCE: 3
aagacttagt acctgaaggg tga                                          23

<210> SEQ ID NO 4
<211> LENGTH: 23
<212> TYPE: DNA
<213> ORGANISM: Artificial Sequence
<220> FEATURE:
<223> OTHER INFORMATION: Synthetic

<400> SEQUENCE: 4
ccttcctctt cctacagtac tcc                                          23

<210> SEQ ID NO 5
<211> LENGTH: 22
<212> TYPE: DNA
<213> ORGANISM: Artificial Sequence
<220> FEATURE:
<223> OTHER INFORMATION: Synthetic

<400> SEQUENCE: 5
ggtcccaaga cttagtacct ga                                           22

<210> SEQ ID NO 6
<211> LENGTH: 21
<212> TYPE: DNA
<213> ORGANISM: Artificial Sequence
<220> FEATURE:
<223> OTHER INFORMATION: Synthetic

<400> SEQUENCE: 6
actccacacg caaatttcct t    21

<210> SEQ ID NO 7
<211> LENGTH: 21
<212> TYPE: DNA
<213> ORGANISM: Artificial Sequence
<220> FEATURE:
<223> OTHER INFORMATION: Synthetic

<400> SEQUENCE: 7
acacgcaaat tccttccac t    21

<210> SEQ ID NO 8
<211> LENGTH: 20
<212> TYPE: DNA
<213> ORGANISM: Artificial Sequence
<220> FEATURE:
<223> OTHER INFORMATION: Synthetic

<400> SEQUENCE: 8
gtgatgatgg tgaggatggg    20

<210> SEQ ID NO 9
<211> LENGTH: 20
<212> TYPE: DNA
<213> ORGANISM: Artificial Sequence
<220> FEATURE:
<223> OTHER INFORMATION: Synthetic

<400> SEQUENCE: 9
cccctcctca gcatcttatc    20

<210> SEQ ID NO 10
<211> LENGTH: 19
<212> TYPE: DNA
<213> ORGANISM: Artificial Sequence
<220> FEATURE:
<223> OTHER INFORMATION: Synthetic

<400> SEQUENCE: 10
taacagttcc tgcatgggc    19

<210> SEQ ID NO 11
<211> LENGTH: 19
<212> TYPE: DNA
<213> ORGANISM: Artificial Sequence
<220> FEATURE:
<223> OTHER INFORMATION: Synthetic

<400> SEQUENCE: 11
acggaacagc tttgaggtg    19

<210> SEQ ID NO 12
<211> LENGTH: 18
<212> TYPE: DNA
<213> ORGANISM: Artificial Sequence
<220> FEATURE:
<223> OTHER INFORMATION: Synthetic

```
<400> SEQUENCE: 12
ccaggacagg cacaaaca                                                    18

<210> SEQ ID NO 13
<211> LENGTH: 18
<212> TYPE: DNA
<213> ORGANISM: Artificial Sequence
<220> FEATURE:
<223> OTHER INFORMATION: Synthetic

<400> SEQUENCE: 13
cagcacatga cggaggtt                                                    18

<210> SEQ ID NO 14
<211> LENGTH: 18
<212> TYPE: DNA
<213> ORGANISM: Artificial Sequence
<220> FEATURE:
<223> OTHER INFORMATION: Synthetic

<400> SEQUENCE: 14
tgtggtggtg ccctatga                                                    18

<210> SEQ ID NO 15
<211> LENGTH: 18
<212> TYPE: DNA
<213> ORGANISM: Artificial Sequence
<220> FEATURE:
<223> OTHER INFORMATION: Synthetic

<400> SEQUENCE: 15
gtgcagctgt gggttgat                                                    18

<210> SEQ ID NO 16
<211> LENGTH: 17
<212> TYPE: DNA
<213> ORGANISM: Artificial Sequence
<220> FEATURE:
<223> OTHER INFORMATION: Synthetic

<400> SEQUENCE: 16
gacggaggtt gtgaggc                                                     17

<210> SEQ ID NO 17
<211> LENGTH: 17
<212> TYPE: DNA
<213> ORGANISM: Artificial Sequence
<220> FEATURE:
<223> OTHER INFORMATION: Synthetic

<400> SEQUENCE: 17
ccaagacctg ccctgtg                                                     17

<210> SEQ ID NO 18
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (18)..(18)
<223> OTHER INFORMATION: n is inosine

<400> SEQUENCE: 18
agcacatgac ggaggttn                                                    18
```

<210> SEQ ID NO 19
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: n is a 5'-C6 thiol linker

<400> SEQUENCE: 19
ngttttccca gtcacgac                                                 18

<210> SEQ ID NO 20
<211> LENGTH: 36
<212> TYPE: PRT
<213> ORGANISM: Artificial Sequence
<220> FEATURE:
<223> OTHER INFORMATION: Synthetic

<400> SEQUENCE: 20

Gly Ala Gly Thr Gly Ser Ala Gly Ala Gly Thr Gly Arg Ala Gly Ala
1               5                   10                  15

Gly Thr Gly Ser Ala Gly Ala Gly Thr Gly Arg Ala Gly Ala Gly Thr
            20                  25                  30

Gly Ser Ala Gly
        35

<210> SEQ ID NO 21
<211> LENGTH: 127
<212> TYPE: PRT
<213> ORGANISM: Artificial Sequence
<220> FEATURE:
<223> OTHER INFORMATION: Synthetic

<400> SEQUENCE: 21

Gly Ala Gly Thr Gly Ser Ala Gly Ala Gly Thr Gly Ser Ala Gly Ala
1               5                   10                  15

Gly Thr Gly Ser Ala Gly Ala Gly Thr Gly Ser Ala Gly Ala Gly Thr
            20                  25                  30

Gly Ser Ala Gly Ala Gly Thr Gly Ser Ala Gly Ala Gly Thr Gly Ser
        35                  40                  45

Ala Gly Ala Gly Thr Gly Ser Ala Gly Ala Gly Thr Gly Ser Ala Gly
    50                  55                  60

Ala Gly Thr Gly Ser Ala Gly Ala Gly Thr Gly Ser Ala Gly Ala Gly
65                  70                  75                  80

Thr Gly Ser Ala Gly Ala Gly Thr Gly Ser Ala Gly Ala Gly Thr Gly
                85                  90                  95

Ser Ala Gly Ala Gly Thr Gly Ser Ala Gly Ala Gly Thr Gly Ser Ala
            100                 105                 110

Gly Ala Gly Thr Gly Ser Ala Gly Ala Gly Thr Gly Ser Ala Gly
        115                 120                 125

<210> SEQ ID NO 22
<211> LENGTH: 127
<212> TYPE: PRT
<213> ORGANISM: Artificial Sequence
<220> FEATURE:
<223> OTHER INFORMATION: Synthetic

<400> SEQUENCE: 22

-continued

```
Gly Ala Gly Thr Gly Ser Ala Gly Ala Gly Thr Gly Ser Ala Gly Ala
1               5                   10                  15
Gly Thr Gly Ser Ala Gly Ala Gly Thr Gly Ser Ala Gly Ala Gly Thr
                20                  25                  30
Gly Arg Ala Gly Ala Gly Thr Gly Ser Ala Gly Ala Gly Thr Gly Ser
            35                  40                  45
Ala Gly Ala Gly Thr Gly Ser Ala Gly Ala Gly Thr Gly Ser Ala Gly
        50                  55                  60
Ala Gly Thr Gly Ser Ala Gly Ala Gly Thr Gly Ser Ala Gly Ala Gly
65                  70                  75                  80
Thr Gly Ser Ala Gly Ala Gly Thr Gly Arg Ala Gly Ala Gly Thr Gly
                85                  90                  95
Ser Ala Gly Ala Gly Thr Gly Ser Ala Gly Ala Gly Thr Gly Ser Ala
            100                 105                 110
Gly Ala Gly Thr Gly Ser Ala Gly Ala Gly Thr Gly Ser Ala Gly
            115                 120                 125
```